United States Patent [19]

Kubiak et al.

[11] Patent Number: 5,756,458
[45] Date of Patent: May 26, 1998

[54] STABILIZED POTENT GRF ANALOGS

[75] Inventors: Teresa M. Kubiak, Richland; Alan R. Friedman, Portage, both of Mich.

[73] Assignee: Pharmacia & Upjohn Company, Kalamazoo, Mich.

[21] Appl. No.: 442,029

[22] Filed: May 16, 1995

Related U.S. Application Data

[63] Continuation of Ser. No. 250,322, May 27, 1994, abandoned, which is a continuation of Ser. No. 119,326, Sep. 9, 1993, abandoned, which is a continuation of Ser. No. 614,170, filed as PCT/US90/02923, May 30, 1990, abandoned, which is a continuation-in-part of Ser. No. 427,868, Oct. 27, 1989, abandoned, which is a continuation-in-part of Ser. No. 368,231, Jun. 16, 1989, abandoned.

[51] Int. Cl.$^6$ ............................ A61K 38/25; C07K 14/60
[52] U.S. Cl. ..................... 514/12; 530/324; 930/120; 930/DIG. 559
[58] Field of Search ................. 514/12, 2; 530/324, 530/325; 930/DIG. 820, DIG. 821, 120, DIG. 559

[56] References Cited

U.S. PATENT DOCUMENTS

| | | | |
|---|---|---|---|
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,622,312 | 11/1986 | Felix et al. | 530/324 |
| 4,626,523 | 12/1986 | Vale, Jr. et al. | 514/12 |
| 4,628,043 | 12/1986 | Spiess et al. | 514/12 |
| 4,649,131 | 3/1987 | Felix et al. | 514/12 |
| 4,689,318 | 8/1987 | Kaiser et al. | 514/12 |
| 4,734,399 | 3/1988 | Felix et al. | 514/12 |
| 4,784,987 | 11/1988 | Rivier | 514/12 |
| 4,843,064 | 6/1989 | Vaughan | 514/12 |

FOREIGN PATENT DOCUMENTS

| | | |
|---|---|---|
| A-2684388 | 6/1989 | Australia. |
| 136475A2 | 10/1985 | European Pat. Off. |
| 0188214 | 1/1986 | European Pat. Off. |
| 0220958 | 10/1986 | European Pat. Off. |
| 0212531 | 3/1987 | European Pat. Off. ........ C07K 7/10 |
| 212531A1 | 3/1987 | European Pat. Off. |
| 216517A2 | 4/1987 | European Pat. Off. |
| 307860A2 | 3/1989 | European Pat. Off. |
| 320785A2 | 6/1989 | European Pat. Off. |
| WO 89/07113 | 8/1989 | WIPO. |
| WO 90/12810 | 11/1990 | WIPO. |
| WO 92/00095 | 1/1992 | WIPO. |

OTHER PUBLICATIONS

Frohman et al. Molecular Endocrinology, vol. 3(10), pp. 1529–1536 (1989).

Guillemin, R., et al., Growth Hormone-Releasing Factor from a Human Pancreatic Tumor That Caused Acromegaly, Science, 218:585–587 (5 Nov. 1982).

Frohman, L.A., et al., Rapid Enzymatic Degradation of Growth Hormone-releasing Hormone by Plasma in Vitro and in Vivo to a Biologically Inactive Product Cleaved at the NH$_2$ Terminus. J. Clin. Invest., 78:906–913 (1986).

(List continued on next page.)

*Primary Examiner*—Jeffrey E. Russel
*Assistant Examiner*—Kathleen Carroll
*Attorney, Agent, or Firm*—William G. Jameson

[57] ABSTRACT

Novel GRF PEPTIDES having Thr, Val or Ile at position 2, having an amino acid selected from the group consisting of Ala, Val, Leu, Ile or Gly at position 15, and optionally substituted with Val or Ile at position 19 are described. Compositions and the method of stimulating the release of growth hormone utilizing GRF PEPTIDES having Thr, Val or Ile at position 2 and having an amino acid selected from the group consisting of Ala, Val, Leu, Ile or Gly at position 15 are also described. The GRF PEPTIDES of the present invention have enhanced stability in plasma.

18 Claims, 2 Drawing Sheets

OTHER PUBLICATIONS

Felix, A.M., et al., Synthesis and biological activity of novel linear and cyclic GRF analogs, Peptides, Chem. & Biology, Proc. 10th Am. Peptide Symposium, Ed. G.R. Marshall, ESCOM Sci. Publishers, Leiden, The Netherlands, pp. 465–467 (1988).

Frohman, L.A., et al., Dipeptidylpeptidase IV and Trypsin-like Enzymatic Degradation of Human Growth Hormone-releasing Hormone in Plasma, J. Clin. Invest., 83:1533–1540 (1989).

Murphy, W.A. and Coy, D.H., Potent Long-Acting Alkylated Analogs of Growth Hormone-Releasing Factor, Peptide Research, 1(No. 1):36–41 (1988).

Ling, N. et al., Synthetic GRF analogs as competitive antagonists of GRF, Quo Vadis? Symposium, Sanofi Group, May 29–30, 1985, Toulouse–Labege, France, pp. 309–322.

Felix, A.M. et al., Synthesis and Biological Activity or Novel Growth Hormone Releasing Factor Analogs, Peptides 1986, Walter de Gruyter & Co., Berlin–New York, pp. 481–484.

Petiticlerc, D. et al., Effect of a potent analog of human growth hormone-releasing factor (hGRF) on growth hormone (GH) release and milk production of dairy cows, 82nd Meeting American Dairy Sci. Assn., Columbia, MO, Abstract P223, Jun. 21–24 (1987).

Tou, J.S. et al., Amphiphilic Growth Hormone Releasing Factor (GRF) Analogs: Peptide Design and Biological Activity In Vivo, Biochem. & Biophys. Res. Commun., 139(No. 2):763–770 (16 Sep. 1986).

Coy, D.H. et al., Strategies in the Design of Synthetic Agonists and Antagonists of Growth Hormone Releasing Facor, Peptides, 7(Suppl.1):49–52 (1986).

Ling, N. et al., Growth hormone-releasing factor analogs with potent antagonist activity, Peptides, Chem. & Biol., Proc. of the 10th Amer. Peptide Symposium, Ed. G.R. Marshall, ESCOM Sci. Publishers, Leiden, The Netherlands (1988), pp. 484–486.

Velicelebi, G. et al., Design and bioligical activity of analogs of growth hormone releasing factor with potential amphiphilic helical carboxyl termini, Proc. Natl Acad. Sci. USA, 83:5397–5399 (Aug. 1986).

Kossiakoff, A.A., Tertiary Structure Is a Principal Determinant to Protein Deamidation, Science 240:191–194 (8(Apr. 1988).

Tallon, M.A. et al., Synthesis and Biological Activity of Amino Terminus Extended Analogues of the β Mating Factor of Saccharomyces cerevisiae, Amer. Chem. Soc., Biochem., 26:7767–7774 (1987).

Andreu, D. et al., Preprocecropin A: Chemical Synthesis and Processing Studies, 20th Eur. Peptide Symposium, Sep. 4–9, 1988, Syposium Abstracts, p.33.

Kreil, G. et al., Stepwise Cleavage of the Pro Part Promelittin by Dipeptdiylpeptidase IV, Eur. J. Biochem., 111:49–58 (1980).

Mollay, et al., Isolation of a dipeptidylaminopeptidase, a putative processing enzyme, from skin secretion of Xenopus laevis, Eur. J. Biochem., 160:31–35 (1986).

Julius, D. et al., Yeast β Factor is Processed from a Larger Precursor Polypeptide: The Essential Role of a Membrane–Bound Dipeptidyl aminopeptidase, Cell, 32:839–852 (Mar. 1983).

Choy, L. et al., Biosynthesis of antifreeze polypeptides in the winter flounder –Characterization and seasonal occurrence of precursor polypeptides, Eur. J. Biochem., 160:267–272 (1986).

Coy, D.H. et al., Structure–Activity Studies on the N-Terminal Region of Growth Hormone Releasing Factor, J. Med. Chem., 28:181–185 (1985).

Schroder & Lubke, The Peptides, Academic Press (:965).* Table of Contents and Nomenclature only; specific pages will be sent upon request.

Application 07/303,518 (Jan. 27, 1989), Friedman.
Application 07/323,955 (Mar. 15, 1989), Friedman.
Application 07/053,233 (May 22, 1987), Vale et al.
Application 07/150,301 (Jan. 29, 1988), Friedman.
Application 89/00245 (Jan. 27, 1989), Friedman.

Boman, H. G., and I. A. Boman, "Chemical Synthesis and Enzymic Processing of Precursor Forms of Cecropins A and B", 1989 J. Biol. Chem. 264(10):5852–5860.

Kempe, T., et al. "Production and Characterization of Growth Hormone Releasing Factor Analogs Through Recombinant DNA and Chemical Techniques", 1986, Bio/Technology 4:565–568.

Sathyamoorthy, V., and B. R. DasGupta, "Reductive Methylation of Lysine Residues of Botulinum Neurotoxin Types A and B", 1988, Mol. Cell. Biochem. 83:65–72.

Moseley, W. M., et al., "Food Intake Alters the Serum Growth Hormone Response to Bovine Growth Hormone–Releasing Factor in Meal–Fed Holstein Steers", 1988, J. Endocr. 117:253–259.

Lapierre, H., et al., "Effect of a potent analog of human growth hormone–releasing factor (hGRF) on growth hormone (GH) release of dairy cows," 82nd Meeting of American Dairy Science Association, Columbia, Missouri, *Abstract P2222*, (21–24 Jun. 1987).

Frohman, M.A., et al. "Cloning and Characterization of Mouse Growth Hormone–Releasing Hormone (GRH) Complementary DNA: Increased GRH Messenger RNA Levels in the Growth Hormone–Deficient lit/lit Mouse," *Molecular Endocrinology*, 3:10 (Oct. 1989), 1529–1536.

Suhr, S.T., et al. "Mouse Growth Hormone–Releasing Hormone: Precursor Structure and Expression in Brain and Placenta," *Molecular Endocrinology*, 3:11 (Nov. 1989), 1693–1700.

Stewart, J.M. and Janis Hillaha Young. *Solid Phase Peptide Synthesis*. 2nd ed. (1984). Pierce Chemical Company:Rockford, Illinois. p. 113.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 31
        ( B ) TYPE: amino acid
        ( D ) TOPOLOGY: linear ( i x ) FEATURE:
        ( A ) NAME/KEY: C-terminally amidated Argininyl residue
        ( B ) LOCATION: Xaa31

( x i ) SEQUENCE DESCRIPTION: SEQ ID NO:1:

```
Tyr Thr Tyr Thr Asp Ala Ile Phe Thr Asn Ser Tyr Arg Lys Val Leu
 1               5                  10                  15
Ala Gln Leu Ser Ala Arg Lys Leu Leu Gln Asp Ile Leu Asn Xaa
            20                  25                  30
```

( 2 ) INFORMATION FOR SEQ ID NO:2:

( i ) SEQUENCE CHARACTERISTICS:
        ( A ) LENGTH: 33
        ( B ) TYPE: amino acid
        ( D ) TOPOLOGY: linear ( i x ) FEATURE:
        ( A ) NAME/KEY: C-terminally amidated Argininyl residue
        ( B ) LOCATION: Xaa33

( x i ) SEQUENCE DESCRIPTION: SEQ ID NO:2:

```
Tyr Thr Tyr Thr Tyr Thr Asp Ala Ile Phe Thr Asn Ser Tyr Arg Lys
 1               5                  10                  15
Val Leu Ala Gln Leu Ser Ala Arg Lys Leu Leu Gln Asp Ile Leu Asn
            20                  25                  30
Xaa
```

( 2 ) INFORMATION FOR SEQ ID NO:3:

( i ) SEQUENCE CHARACTERISTICS:
        ( A ) LENGTH: 31
        ( B ) TYPE: amino acid
        ( D ) TOPOLOGY: linear ( i x ) FEATURE:
        ( A ) NAME/KEY: C-terminally amidated Argininyl residue
        ( B ) LOCATION: Xaa31

( x i ) SEQUENCE DESCRIPTION: SEQ ID NO:3:

```
Tyr Thr Tyr Ala Asp Ala Ile Phe Thr Asn Ser Tyr Arg Lys Val Leu
 1               5                  10                  15
Ala Gln Leu Ser Ala Arg Lys Leu Leu Gln Asp Ile Leu Asn Xaa
            20                  25                  30
```

( 2 ) INFORMATION FOR SEQ ID NO:4:

( i ) SEQUENCE CHARACTERISTICS:
        ( A ) LENGTH: 31

(B) TYPE: amino acid
(D) TOPOLOGY: linear (ix) FEATURE:
(A) NAME/KEY: C-terminally amidated Argininyl residue
(B) LOCATION: Xaa31

(xi) SEQUENCE DESCRIPTION: SEQ ID NO:4:

| Tyr | Thr | Tyr | Ile | Asp | Ala | Ile | Phe | Thr | Asn | Ser | Tyr | Arg | Lys | Val | Leu |
|---|---|---|---|---|---|---|---|---|---|---|---|---|---|---|---|
| 1 | | | | 5 | | | | | 10 | | | | | 15 | |

| Ala | Gln | Leu | Ser | Ala | Arg | Lys | Leu | Leu | Gln | Asp | Ile | Leu | Asn | Xaa |
|---|---|---|---|---|---|---|---|---|---|---|---|---|---|---|
| | | | 20 | | | | | 25 | | | | | 30 | |

(2) INFORMATION FOR SEQ ID NO:5:

(i) SEQUENCE CHARACTERISTICS:
(A) LENGTH: 31
(B) TYPE: amino acid
(D) TOPOLOGY: linear (ix) FEATURE:
(A) NAME/KEY: C-terminally amidated Argininyl residue
(B) LOCATION: Xaa31

(xi) SEQUENCE DESCRIPTION: SEQ ID NO:5:

| Tyr | Ser | Tyr | Thr | Asp | Ala | Ile | Phe | Thr | Asn | Ser | Tyr | Arg | Lys | Val | Leu |
|---|---|---|---|---|---|---|---|---|---|---|---|---|---|---|---|
| 1 | | | | 5 | | | | | 10 | | | | | 15 | |

| Ala | Gln | Leu | Ser | Ala | Arg | Lys | Leu | Leu | Gln | Asp | Ile | Leu | Asn | Xaa |
|---|---|---|---|---|---|---|---|---|---|---|---|---|---|---|
| | | | 20 | | | | | 25 | | | | | 30 | |

(2) INFORMATION FOR SEQ ID NO:6:

(i) SEQUENCE CHARACTERISTICS:
(A) LENGTH: 45
(B) TYPE: amino acid
(D) TOPOLOGY: linear (ix) FEATURE:
(A) NAME/KEY: C-terminally amidated homoserine residue
(B) LOCATION: Xaa45

(xi) SEQUENCE DESCRIPTION: SEQ ID NO:6:

| Tyr | Val | Asp | Ala | Ile | Phe | Thr | Ser | Ser | Tyr | Arg | Lys | Val | Leu | Ala | Gln |
|---|---|---|---|---|---|---|---|---|---|---|---|---|---|---|---|
| 1 | | | | 5 | | | | | 10 | | | | | 15 | |

| Leu | Ser | Ala | Arg | Lys | Leu | Leu | Gln | Asp | Ile | Leu | Ser | Arg | Gln | Gln | Gly |
|---|---|---|---|---|---|---|---|---|---|---|---|---|---|---|---|
| | | | 20 | | | | | 25 | | | | | 30 | | |

| Glu | Arg | Asn | Gln | Glu | Gln | Gly | Ala | Lys | Val | Arg | Leu | Xaa |
|---|---|---|---|---|---|---|---|---|---|---|---|---|
| | | 35 | | | | | 40 | | | | | 45 |

(2) INFORMATION FOR SEQ ID NO:7:

(i) SEQUENCE CHARACTERISTICS:
(A) LENGTH: 33
(B) TYPE: amino acid
(D) TOPOLOGY: linear (ix) FEATURE:
(A) NAME/KEY: C-terminally amidated homoserine residue
(B) LOCATION: Xaa33

(xi) SEQUENCE DESCRIPTION: SEQ ID NO:7:

| Tyr | Val | Asp | Ala | Ile | Phe | Thr | Ser | Ser | Tyr | Arg | Lys | Val | Leu | Ala | Gln |
|---|---|---|---|---|---|---|---|---|---|---|---|---|---|---|---|
| 1 | | | | 5 | | | | | 10 | | | | | 15 | |

| Leu | Ser | Ala | Arg | Lys | Leu | Leu | Gln | Asp | Ile | Leu | Ser | Arg | Gln | Gln | Gly |
|---|---|---|---|---|---|---|---|---|---|---|---|---|---|---|---|
| | | | 20 | | | | | 25 | | | | | 30 | | |

Xaa ( 2 ) INFORMATION FOR SEQ ID NO:8:

( i ) SEQUENCE CHARACTERISTICS:
        ( A ) LENGTH: 30
        ( B ) TYPE: amino acid
        ( D ) TOPOLOGY: linear ( i x ) FEATURE:
        ( A ) NAME/KEY: C-terminally amidated homoserine residue
        ( B ) LOCATION: Xaa30

( x i ) SEQUENCE DESCRIPTION: SEQ ID NO:8:

```
Tyr Val Asp Ala Ile Phe Thr Ser Ser Tyr Arg Lys Val Leu Ala Gln
 1               5                  10                  15
Leu Ser Ala Arg Lys Leu Leu Gln Asp Ile Leu Ser Arg Xaa
            20                  25                  30
```

( 2 ) INFORMATION FOR SEQ ID NO:9:

( i ) SEQUENCE CHARACTERISTICS:
        ( A ) LENGTH: 28
        ( B ) TYPE: amino acid
        ( D ) TOPOLOGY: linear ( i x ) FEATURE:
        ( A ) NAME/KEY: C-terminally amidated homoserine residue
        ( B ) LOCATION: Xaa28

( x i ) SEQUENCE DESCRIPTION: SEQ ID NO:9:

```
Tyr Val Asp Ala Ile Phe Thr Ser Ser Tyr Arg Lys Val Leu Ala Gln
 1               5                  10                  15
Leu Ser Ala Arg Lys Leu Leu Gln Asp Ile Leu Xaa
            20                  25
```

( 2 ) INFORMATION FOR SEQ ID NO:10:

( i ) SEQUENCE CHARACTERISTICS:
        ( A ) LENGTH: 29
        ( B ) TYPE: amino acid
        ( D ) TOPOLOGY: linear ( i x ) FEATURE:
        ( A ) NAME/KEY: C-terminally amidated Argininyl residue
        ( B ) LOCATION: Xaa29

( x i ) SEQUENCE DESCRIPTION: SEQ ID NO:10:

```
Tyr Thr Asp Ala Ile Phe Thr Asn Ser Tyr Arg Lys Val Leu Ala Gln
 1               5                  10                  15
Leu Ser Val Arg Lys Leu Leu Gln Asp Ile Leu Asn Xaa
            20                  25
```

( 2 ) INFORMATION FOR SEQ ID NO:11:

( i ) SEQUENCE CHARACTERISTICS:
        ( A ) LENGTH: 29
        ( B ) TYPE: amino acid
        ( D ) TOPOLOGY: linear ( i x ) FEATURE:
        ( A ) NAME/KEY: C-terminally amidated Argininyl residue
        ( B ) LOCATION: Xaa29

( x i ) SEQUENCE DESCRIPTION: SEQ ID NO:11:

```
Tyr Thr Asp Ala Ile Phe Thr Asn Ser Tyr Arg Lys Val Leu Ala Gln
 1               5                  10                  15
Leu Ser Ile Arg Lys Leu Leu Gln Asp Ile Leu Asn Xaa
            20                  25
```

(2) INFORMATION FOR SEQ ID NO:12:

(i) SEQUENCE CHARACTERISTICS:
      (A) LENGTH: 29
      (B) TYPE: amino acid
      (D) TOPOLOGY: linear (ix) FEATURE:
      (A) NAME/KEY: C-terminally amidated Argininyl residue
      (B) LOCATION: Xaa29

(xi) SEQUENCE DESCRIPTION: SEQ ID NO:12:

Tyr Thr Asp Ala Ile Phe Thr Asn Ser Tyr Arg Lys Val Leu Ala Gln
 1               5                  10                  15

Leu Ser Leu Arg Lys Leu Leu Gln Asp Ile Leu Asn Xaa
            20                  25

STABILIZED POTENT GRF ANALOGS

CROSS REFERENCE TO RELATED PATENT APPLICATIONS

This application is a continuation of U.S. Ser. No. 08/250,322, filed 27 May, 1994 now abandoned; which is a continuation of U.S. Ser. No. 08/119,326, filed 9 Sep., 1993 now abandoned; which is a continuation of U.S. Ser. No. 07/614,170, filed Nov. 14, 1990 now abandoned; which is a continuation-in-part of International Patent Application No. PCT/US90/02923, filed May 30, 1990; which is a continuation-in-part of U.S. Ser. No. 07/427,868, filed Oct. 27, 1989 now abandoned; which is a continuation-in-part of U.S. Ser. No. 07/368,231, filed Jun. 16, 1989, abandoned.

INTRODUCTION

The present invention relates to a peptide having influence on the function of the pituitary gland in humans and other animals, particularly mammals. In particular, the present invention is directed to peptides which promote the release of growth hormone by the pituitary gland. The peptides of the present invention are potent in vivo, more stable in plasma and selected peptides are more stable in an aqueous environment at neutral pH than native GRF sequences.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. In 1982, human pancreatic (tumor) releasing factors (hpGRF) were isolated from extracts of human pancreatic tumors, purified, characterized, synthesized, tested, and found to promote release of growth hormone (GH) by the pituitary. Guillemin, R., et al., Science 218, 585–587 (1982). Since then, corresponding hypothalamic GH releasing factors from other species including the rat species, the porcine species, the ovine species, the bovine and caprine species and from the human species have also been characterized and synthesized.

Human hypothalamic GRF (hGRF) has been found to have the same formula as hpGRF, namely: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-$NH_2$.

Rat GRF (rGRF) has been found to have a Ser residue at position 8 and the formula: H-His-Ala-Asp-Ala-Ile-Phe-Thr-Ser-Ser-Tyr-Arg-Arg-Ile-Leu-Gly-Gln-Leu-Tyr-Ala-Arg-Lys-Leu-Leu-His-Glu-Ile-Met-Asn-Arg-Gln-Gln-Gly-Glu-Arg-Asn-Gln-Glu-Gln-Arg-Ser-Arg-Phe-Asn-OH. (See for example U.S. Pat. No. 4,595,676).

Bovine GRF (bGRF) has been found to have the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-$NH_2$.

Porcine GRF has been found to have a Ser residue at position 28.

It has been reported that native GRF sequences are subject to rapid inactivation by blood plasma enzymes. The rapid breakdown involves cleavage of the 2–3 bond of the peptide by a dipeptidylpeptidase, Type IV (DPP-IV), which in the past was also named dipeptidylaminopeptidase-IV. Frohman, L. A. et al., J. Clin. Invest., 78, 906–913 (1986).

The metabolic stability of GRF and various methods for protecting GRF peptides against dipeptidylpeptidase cleavage have been proposed, including Felix et al., Synthesis and biological activity of novel linear and cyclic GRF analogs, in Peptides, Chemistry and Biology, Proc. 10th Am. Peptide Symposium, Ed. G. R. Marshall, ESCOM Sci. Publishers, Leiden, The Netherland, pp.465–467, (1988), who reported on GRF analogs substituted with desNH2-Tyr at position 1, or/and D-Ala at position 2 which had enhanced stability of their N-termini to enzymatic degradation. This information was recently confirmed by Frohman et al., Dipeptidylpeptidase-IV and trypsin-like enzymatic degradation of human growth hormone-releasing hormone in plasma. J. Clin. Invest. 83, 1533–1540 (1989). In addition, the latter group showed that N-acetylation and N-methylation of the N-terminal tyrosine residue or substitution with D-Tyr-1 in GRF completely inhibited cleavage at the 2–3 position. On the other hand, alpha-methylation of Tyr-1, only partially blocked degradation by DPP-IV.

Murphy, W. A. and Coy, D. H., Potent long-acting alkylated analogs of growth hormone-releasing factor, Peptide Research 1, 36–41 (1988), describe analogs of GRF which show enhanced resistance to enzymatic degradation as a result of N-alkylation or N-arylalkylation of the N-terminal amino acid with or without concomitant N-alkylation of the side groups of lysines within the peptide chain.

Native GRF sequences have a Gly residue at the 15-position. Analogs with Ala or Leu at the 15-position are known to have increased GH releasing potency. See for example U.S. Pat. Nos. 4,649,131 and 4,734,399 as well as Ling, N., et al., Quo Vadis?, Symposium, Sanofi Group, May 29–30, 1985, Toulouse-Labege, France (pp. 309–322). Substitutions of Gly-15 with Val or alpha-amino-isobutyric acid also resulted in enhanced potency of GRF analogs. Felix et al., Synthesis and biological activity of novel growth hormone releasing factor analogs, in Peptides 1986, Walter de Gruyter & Co., Berlin, N.Y., pp. 481–484 (1987).

A. M. Felix has reported on a program to synthesize analogs with enhanced and/or prolonged biological activity, including the preparation and testing of $Ala^{15}$ h-GRF(1–29)$NH_2$ and $desNH_2$-$Tyr^1$, D-$Ala^2$, $Ala^{15}$ hGRF(1–29)$NH_2$. See, for example, U.S. Pat. Nos. 4,649,131 and 4,734,399 as well as A. M. Felix, E. P. Heimer, T. F. Mowles, H. Bisenbeis, P. Leung, T. J. Lambros, M. Ahmad, C.-T. Wang & Paul Brazeau: Synthesis and biological activity of novel growth hormone releasing factor analogs, in Peptides 1986, pp. 481–484 (1987); Felix, A. M., Wang, C. T., Heimer, E., Fournier, A., Bolin, D., Ahmad, M., Lambros, T., Mowles, T., and Miller, L.: Synthesis and biological activity of novel linear and cyclic GRF analogs, in Peptides, Chemistry and Biology, Proceedings of the 10th American Peptide Symposium, Ed. G. R. Marshall, Escom Science Publishers, Leiden, The Netherlands (1988), pp. 465–467; D. Peticlerc, H. Lapierre, G. Pelletier, P. Dubreuil, P. Gaudreau, T. Mowles, A. Felix and P. Brazeau: Effect of a potent analog of human growth hormone-releasing factor (hGRF) on growth hormone (GH) release and milk production of dairy cows. Meeting Abstract P223, 82nd Meeting American Dairy Sci. Assn., Columbia, Mo., Jun. 21–24 (1987).

A GRF analog that was modified with $Ser^2$, in addition to eight other modifications in the same molecule, is described by Tou et al., Amphiphilic Growth Hormone-Releasing Factor (GRF) analogs: peptide design and biological activity in vivo. Biochem. Biophys. Res. Commun. 139, 763–770 (1986). This analog was reported to have 165% activity in vivo in sheep as compared to bGRF(1–44)$NH_2$.

U.S. Pat. No. 4,734,399 discloses GRF analogs having Ala, N-Methyl-D-Ala or D-Ala at position 2 and Ala, Leu, Val, Ile, Nle, Nval or β-Ala at position 15. See also U.S. Pat. No. 4,649,131.

European Patent Application of Coy and Murphy, Publication Number 0 188 214, Application Number 86100127.9, discloses GRF analogs with Leu or Phe at position 2, in addition to GRF peptides having various unnatural amino acids of L or D-configuration as substituents at position 2.

GRF analogs with very low bioactivity having Sar$^2$ or Pro$^2$ are described by Coy et al., Strategies in the design of synthetic agonists and antagonists of growth hormone-releasing factor, Peptides, vol. 7, Suppl. 49–52 (1986).

Ling et al., Growth hormone-releasing factor analogs with potent antagonistic activity, in Peptides, Chemistry and Biology, Proceedings of the 10th American Peptide Symposium, Ed. G. R. Marshall, Escom Science Publishers, Leiden, The Netherlands (1988), pp. 484–486, reported on a series of GRF analogs substituted with either Arg or a variety of D-amino acids at position 2. All of them are less potent than the parent hormone and some of them displayed antagonistic activity.

The prior invention of a co-worker provides synthetic GRF polypeptides having a Ser residue in place of the amino acid residue normally found at position 8 and 28 of the polypeptide as a means of inhibiting chemical breakdown (deamidation) in aqueous environments. See U.S. patent application Ser. No. 07/303,518, filed 27 Jan., 1989 and Ser. No. 07/323,955, filed 15 Mar., 1989.

The prior invention of a co-worker provides synthetic GRF polypeptides having a cysteic acid residue (Cya) substituted for the amino acid residue in position $R_3$ and/or $R_{25}$. See U.S. patent application Ser. No. 07/150,301, filed 29 Jan., 1988, now abandoned, and Ser. No. 89/00245, filed 27 Jan., 1989 (International Publication 89/07113, published Aug. 10, 1989) and the national phase U.S. Ser. No. 07/844,988, filed Mar. 2, 1992, now abandoned.

A 29-amino acid analog of hGRF was designed by G. Velicelebi, et al., Proc. Natl. Aca. Sci USA, Vol 83, 5397–5399 (1986), in which the sequence of the first six amino acids at the amino terminus, and differing from the natural peptide by 13 amino acid in the rest of the sequence including incorporation of a Ser residue at position 8. The amide and free acid forms of the analog had the formula: H-Tyr-Ala-Asp-Ala-Ile-Phe-Ser-Ser-Ala-Tyr-Arg-Arg-Leu-Leu-Ala-Gln-Leu-Ala-Ser-Arg-Arg-Leu-Leu-Gln-Glu-Leu-Leu-Ala-Arg-NH$_2$/OH. When assayed for the ability to stimulate growth hormone (GH) secretion in primary cultures of rat anterior pituitary cells, the amide analog was 1.57 times as potent as hGRF(1–40)OH, while the free acid form was reported to be ⅙th as potent in the same assay.

Vale, et al., (U.S. patent application Ser. No. 07/053,233, filed May 22, 1987, now abandoned) describe 31-residue hGRF analogues which utilize a 31-position residue possessing a functional side chain group which may be conjugated to a separate protein. The 31-residue hGRF analogues may also have substitutions for other residues which appear in a natural GRF sequence, such as Asn or Ser in the 8-position, Phe in the 10-position, or Ala in the 15-position. Asn or Ser may be present in the 28-position.

Asn residues in polypeptides are reported to be the subject, under some circumstances, to deamidation in the presence of water. However, the rules governing the rates of deamidation are not clear. For example, in the polypeptide trypsin only some of the Asn residues, with the partial sequence Asn-Ser, are deamidated while others are not. See Kossiakoff, A A, Science 240, 191–194 (1988).

European Patent Application Number 86308337.4, Publication number 0 220 958, discloses a class of compounds having the formula H-X-Pro-Peptide in which X is the residue of a naturally occurring amino acid, Pro refers to the naturally occurring amino acid proline and Peptide is a sequence of amino acid residues defining that of a biologically active peptide or protein. Examples of H-X-Pro-Peptide include Met-Pro- (growth hormone-releasing factor) which can be chemically converted to GRF.

N-terminally extended analogs on non-GRF peptides have been reported for various purposes including, for example:

M. A. Tallon et al., Biochem., 26:7767–7774 (1987), made synthetically a series of N-terminally extended analogs of yeast alpha-mating factor with Ala, Glu-Ala, Ala-Glu-Ala or Glu-Ala-Glu-Ala in the extension part. These peptides were used in structure-activity relationship studies.

D. Andreu et al., 20th Eur. Peptide Symp., Tubingen, GFR, Sep. 4–9, 1988, Symposium Abstracts, p. 33, synthesized the entire 64-amino acid sequence of the precursor form of cecropin A along with several shorter peptides corresponding to potential processing intermediates. Among them there was a full cecropin sequence extended with Ala-Pro-Gly-Pro at its N-terminus which was used to show that the extension part was indeed cleaved by a partially purified dipeptidylpeptidase-like enzymatic preparation obtained from the cecropia silkmoth pupa. See also H. Boman et al. J. Biol. Chem. 264:5852–5860 (1989).

G. Kreil et al., Eur. J. Biochem., 111:49–58 (1980) reports that melittin, the main constituent of honeybee venom, is derived from pro-melittin. The pro-sequence of pro-melittin consists of six X-Pro and five X-Ala repetitive dipeptidyl residues. The results presented by Kreil et al. suggest that the precursor-product conversion may proceed via stepwise cleavage of dipeptide units by a dipeptidylpeptidase IV type enzyme present in extracts from venom glands.

C. Mollay et al., Eur. J. Biochem., 160:31–35 (1986). Caerulein and xenopsin are two peptides found in skin secretion of *Xenopus laevis*. The former has a sequence of Phe-Ala-Asp-Gly and the latter Ser-Ala-Glu-Ala in the N-terminal extensions in their respective precursor forms. A dipeptidylpeptidase of type IV, isolated from frog skin secretion, has the specificity required for the cleavage of these N-terminal extensions leading to the formation of the mature products.

D. Julius et al., Cell, 32:839–852 (1983). Alpha factor mating pheromone is a peptide of 13 amino acids secreted by *Saccharomyces cervisiae* alpha cells. Nonmating alpha-cell mutants, which lack a membrane-bound dipeptidylpeptidase, do not produce normal alpha-factor, but release a collection of incompletely processed forms with structures Glu-Ala-Glu-Ala-alpha-factor or Asp-Ala-Glu-Ala-alpha-factor that have a markedly reduced biological activity. It has been shown that the membrane-bound dipeptidylpeptidase is required for normal alpha-factor precursor processing and this process may be rate-limiting for alpha-factor maturation in normal yeast alpha cells.

C. L. Choy et al., Eur. J. Biochem., 160:267–272 (1986). The prosequence of the antifreeze protein from the Newfoundland winter flounder contains four X-Pro and seven X-Ala repetitive sequences in its N-terminal part. Although the processing of this precursor has not been investigated, the authors speculate that such a conversion might take place in serum by a dipeptidylpeptidase-line enzyme which would sequentially cleave the dipeptidyl units in the extension part to release the mature antifreeze protein.

Subsequent to the priority date of the parent application, Suhr et. al. reported the isolation and characterization of a full-length cDNA clone encoding mouse GRF. The mature mouse GRF was predicted to be a 42 amino acid residue peptide with a free carboxyl-terminus. This peptide has a valine residue at position 2 which makes it unique among the GRFs from other species all having Ala at position 2. See Mol. Endocrinology 3: 1693–1700, 1989.

SUMMARY OF THE INVENTION

The present invention provides a synthetic polypeptide which promotes the release of growth hormone by the pituitary gland (GRF PEPTIDE) and having Thr, Val or Ile residue in place of the amino acid residue normally found at position 2 in combination with one of the following amino acids Ala, Val, Leu, Ile or Gly at position 15. Optionally, the GRF PEPTIDE can have a Ser residue in place of the amino acid residue normally found at position 8 and 28 of the polypeptide. In addition, the GRF PEPTIDES of the present invention can optionally be N-terminally extended with $C_1$–$C_5$ alkyl, benzyl, H—$(Y—X)_n$ or H—$(Y—X)_m(Y'—X')_p$ wherein Y and Y', being the same or different, is a naturally occurring amino acid, preferably Tyr or Asp; X and X', being the same or different, is selected from Thr, Ser or Ala, preferably Thr or Ser; n is 1–10; m is 1–5; p is 1–5.

The peptides of the present invention are potent in vivo and more stable than native GRF sequences against breakdown by blood plasma enzymes. In addition, compounds substituted with $Ser^8$ and $Ser^{28}$ are protected against deamidation in aqueous environments and are chemically more stable.

DETAILED DESCRIPTION OF THE INVENTION

The term "GRF PEPTIDE", as used in the specification and claims, means a known polypeptide which is between 27 and 44 residues in length and that promotes the release of growth hormone by the pituitary gland. Illustrative GRF PEPTIDES include the natural or synthetic polypeptides disclosed in U.S. Pat. Nos. 4,517,181, 4,518,586, 4,528,190, 4,529,595, 4,563,352, 4,585,756, 4,595,676, 4,605,643, 4,610,976, 4,626,523, 4,628,043, 4,689,318, 4,784,987, 4,843,064 and U.S. patent application Ser. No. 89/00245, filed 27 Jan., 1989; all of which are incorporated herein by reference. Felix, A., Wang, C. T., Heimer, E., Fournier, A., Bolin, D., Ahmed, M., Lambros, T., Mowles, T., and Miller, L., "Synthesis and Biological Activity of Novel Linear & Cyclic GRF Analogs", in Peptides. Chemistry and Biology, Proc. 10th Am. Peptide Symposium, Ed. G. R. Marshall, ESCOM Sci. Publishers, Leiden, The Netherland, pp.465–467, (1988); Tou, J. S., Kaempfe, L. A., Vineyard, B. D., Buonomo, F. C., Della-Fera, M. A., and Baile, C. A., "Amphiphilic Growth Hormone Releasing Factor Analogs. Peptide Design and Biological Activity in vivo", Biochem. Biophys. Res. Commun. 139 #2, pp. 763–770 (1986); Coy, D. H., Murphy, W. A., Sueires-Diaz, J., Coy, E. J., Lance, V. A., "Structure Activity Studies on the N-Terminal Region of Growth Hormone Releasing Factor", J. Med. Chem. 28, pp. 181–185 (1985); Felix, A. M., Heimer, E. P., Mowles, T. F., Eisenbeis, H., Leung, P., Lambros, T. J., Ahmed, M., and Wang, C. T., "Synthesis and Biological Activity of Novel Growth Hormone Releasing Factor Analogs", in Peptides 1986, Walter de Gruyter & Co., Berlin, N.Y., pp. 481–484 (1987); Velicelebi, G., Patthi, S., and Kaiser, E. T., "Design and Biological Activity of Analogs of Growth Hormone Releasing Factor with Potential Amphiphilic Helical Carboxyl Termini", Proc. Natl. Acad. Sci. U.S.A., 85, pp. 5397–5399 (1986); Ling, N., Baird, A., Wehrenberg, W. B., Munegumi, T., and Ueno, N., "Synthesis GRF Analogs as Competitive Antagonists of GRF Therapeutic Agents Produced by Genetic Engineering", Quo Vadis Symposium, Sanofi Group, May 29–30, 1985, Toulouse-Labege, France, pp. 309–329. Murphy, W. A. and Coy, D. H., Potent longacting alkylated analogs of growth hormone-releasing factor, Peptide Research 1, 36–41 (1988). J. C Tou, L. A. Kaempfe, B. D. Vineyard, F. C. Buonomo, M. A. Della-Fera and C. A. Baile: Amphiphilic Growth Hormone-Releasing Factor (GRF) analogs: peptide design and biological activity in vivo. Biochem. Biophys. Res. Commun. 139, 763–770 (1986). The term GRF PEPTIDE includes nontoxic salts thereof.

The nomenclature used to define the GRF PEPTIDE is that specified by Schroder & Lubke, "The Peptides", Academic Press (1965) wherein in accordance with conventional representation the amino group at the N-terminal appears to the left and the carboxyl group at the C-terminal to the right. Where the amino acid residue has isomeric forms, the L-form of the amino acid is being represented unless otherwise expressly indicated.

The present invention provides synthetic GRF peptide analogs (GRF PEPTIDES) having the following formula:

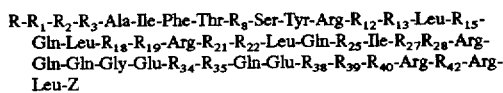

wherein

R is H, $C_1$–$C_5$ alkyl or benzyl;

$R_1$ is Tyr or His, preferably Tyr;

$R_2$ is Thr, Val or Ile, preferably Val or Ile;

$R_3$ is Asp, Glu or Cya, preferably Asp;

$R_8$ is Asn or Ser, preferably Ser;

$R_{12}$ is Lys, N-ε-alkyl- or N-ε-benzyl-Lys or Arg, preferably Lys; or N-ε-alkyl- or N-ε-benzyl-Lys when R is $C_1$–$C_5$ alkyl or benzyl;

$R_{13}$ is Val or Ile, preferably Val;

$R_{15}$ is Ala, Val, Leu, Ile or Gly (preferably Ala, Val, Leu or Ile, more preferably Ala);

$R_{18}$ is Ser or Tyr, preferably Ser;

$R_{19}$ is Ala, Val or Ile (preferably Ala or Val);

$R_{21}$ is Lys, N-ε-alkyl- or N-ε-benzyl-Lys or Arg, preferably Lys or N-ε-alkyl- or N-ε-benzyl-Lys when R is $C_1$–$C_5$ alkyl or benzyl;

$R_{22}$ is Ala or Leu, preferably Leu;

$R_{25}$ is Asp or Glu, preferably Asp;

$R_{27}$ is Met, Ile or Leu, preferably Leu or Ile;

$R_{28}$ is Asn or Ser, preferably Ser;

$R_{34}$ is Ser or Arg, preferably Arg;

$R_{35}$ is Asn or Ser, preferably Asn;

$R_{38}$ is Arg or Gln, preferably Gln;

$R_{39}$ is Gly or Arg, preferably Gly;

$R_{40}$ is Ala or Ser, preferably Ala;

$R_{42}$ is Ala, Val or Phe, preferably Val; and

Z signifies the carboxyl moiety of the amino acid residue at the C-terminal and is the radical —$COOR_a$, —$CR_aO$, —$CONHNHR_a$, —$CON(R_a)(R_b)$ or —$CH_2OR_a$, with $R_a$ and $R_b$ being $C_1$–$C_8$ alkyl or hydrogen; or a biologically active fragment thereof extending from R at the N-terminus to a residue in any of positions 27 through 44 as its C-terminus; or a Hse(lactone), HseOH or HseN($R_a$)($R_b$) of the foregoing and/or a non-toxic salt of the foregoing.

R is preferably hydrogen (H).

Examples of $C_1$-$C_8$ alkyl are methyl, ethyl, propyl, butyl, pentyl, hexyl, octyl and isomeric forms thereof.

The term iPr refers to isopropyl.

In the Sequence Listing Section, some amino acid residues have been designated Xaa in Seq. ID. The following descriptions apply:

In Seq ID No. 1 $Xaa^{31}$ represents C-terminally amidated Argininyl residue.

In Seq ID No. 2 $Xaa^{33}$ represents C-terminally amidated Argininyl residue.

In Seq ID No. 3 $Xaa^{31}$ represents C-terminally amidated Argininyl residue.

In Seq ID No. 4 $Xaa^{31}$ represents C-terminally amidated Argininyl residue.

In Seq ID No. 5 $Xaa^{31}$ represents C-terminally amidated Argininyl residue.

In Seq ID No. 6 $Xaa^{45}$ represents C-terminally amidated Homoserine residue.

In Seq ID No. 7 $Xaa^{33}$ represents C-terminally amidated Homoserine residue.

In Seq ID No. 8 $Xaa^{30}$ represents C-terminally amidated Homoserine residue.

In Seq ID No. 9 $Xaa^{28}$ represents C-terminally amidated Homoserine residue.

In Seq ID No. 10 $Xaa^{29}$ represents C-terminally amidated Argininyl residue.

In Seq ID No. 11 $Xaa^{29}$ represents C-terminally amidated Argininyl residue.

In Seq ID No. 12 $Xaa^{29}$ represents C-terminally amidated Argininyl residue.

The term Bzl refers to benzyl.

An embodiment of this invention is the peptide $Thr^2$ $Ala^{15}$ $Leu^{27}$ bGRF(1–29)$NH_2$ having the formula: H-Tyr-Thr-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-$NH_2$.

A further embodiment of this invention is the peptide $Val^2$ $Ala^{15}$ $Leu^{27}$ bGRF(1–29)$NH_2$ having the formula: H-Tyr-Val-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-$NH_2$.

Still another embodiment of this invention is the peptide $Ile^2$ $Ala^{15}$ $Leu^{27}$ bGRF(1–29)$NH_2$ having the formula: H-Tyr-Ile-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-$NH_2$.

A further embodiment of this invention is the peptide $Thr^2$ $Ser^8$ $Ala^{15}$ $Leu^{27}$ $Ser^{28}$ bGRF(1–44)$NH_2$ having the formula: H-Tyr-Thr-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Gln-Gln-Gly-Glu-Arg-Asn-Gln-Glu-Gln-Gly-Ala-Lys-Val-Arg-Leu-$NH_2$.

Preferred embodiments of this invention are the peptides $Val^2$ $Ser^8$ $Ala^{15}$ $Leu^{27}$ $Ser^{28}$ $Hse^{30}$ bGRF(1–30)$NH_2$, $Val^2$ $Ser^8$ $Ala^{15}$ $Leu^{27}$ $Ser^{28}$ $Hse^{30}$ bGRF(1–30)NH—$C_2H_5$, $Ile^2$ $Ser^8$ $Ala^{15}$ $Leu^{27}$ $Ser^{28}$ $Hse^{30}$ bGRF(1–30)$NH_2$, $Ile^2$ $Ser^8$ $Ala^{15}$ $Leu^{27}$ $Ser^{28}$ $Hse^{30}$ bGRF(1–30)NH—$C_2H_5$, $Val^2$ $Ser^8$ $Ala^{15}$ $Leu^{27}$ $Ser^{28}$ $Hse^{33}$ bGRF(1–33)$NH_2$, $Val^2$ $Ser^8$ $Ala^{15}$ $Leu^{27}$ $Ser^{28}$ $Hse^{33}$ bGRF(1–33)NH—$C_2H_5$, $Ile^2$ $Ser^8$ $Ala^{15}$ $Leu^{27}$ $Ser^{28}$ $Hse^{33}$ bGRF(1–33)$NH_2$, $Ile^2$ $Ser^8$ $Ala^{15}$ $Leu^{27}$ $Ser^{28}$ $Hse^{33}$ bGRF(1–33)NH—$C_2H_5$, $Thr^2$ $Ser^8$ $Ala^{15}$ $Leu^{27}$ $Ser^{28}$ $Hse^{30}$ bGRF(1–30)$NH_2$, $Thr^2$ $Ser^8$ $Ala^{15}$ $Leu^{27}$ $Ser^{28}$ $Hse^{30}$ bGRF(1–30)NH—$C_2H_5$, $Thr^2$ $Ser^8$ $Ala^{15}$ $Leu^{27}$ $Ser^{28}$ $Hse^{33}$ bGRF(1–33)$NH_2$, $Thr^2$ $Ser^8$ $Ala^{15}$ $Leu^{27}$ $Ser^{28}$ $Hse^{33}$ bGRF(1–33) NH—$C_2H_5$, $Val^2$ $Ser^8$ $Ala^{15}$ $Leu^{27}$ $Hse^{28}$ bGRF(1–28)$NH_2$, $Val^2$ $Ser^8$ $Ala^{15}$ $Leu^{27}$ $Hse^{28}$ bGRF(1–28) NH—$C_2H_5$, $Ile^2$ $Ser^8$ $Ala^{15}$ $Leu^{27}$ $Hse^{28}$ bGRF(1–28)$NH_2$, $Ile^2$ $Ser^8$ $Ala^{15}$ $Leu^{27}$ $Hse^{28}$ bGRF(1–28)NH—$C_2H_5$, $Thr^2$ $Ser^8$ $Ala^{15}$ $Leu^{27}$ $Hse^{28}$ bGRF(1–28)$NH_2$, $Thr^2$ $Ser^8$ $Ala^{15}$ $Leu^{27}$ $Hse^{28}$ bGRF(1–28)NH—$C_2H_5$, or a non-toxic salt thereof.

More preferred embodiments of this invention are the peptides $Val^2$ $Ser^8$ $Ala^{15}$ $Leu^{27}$ $Ser^{28}$ $Hse^{30}$ bGRF(1–30) $NH_2$, $Val^2$ $Ser^8$ $Ala^{15}$ $Leu^{27}$ $Ser^{28}$ $Hse^{30}$ bGRF(1–30)NH—$C_2H_5$, $Ile^2$ $Ser^8$ $Ala^{15}$ $Leu^{27}$ $Ser^{28}$ $Hse^{30}$ bGRF(1–30)$NH_2$, $Ile^2$ $Ser^8$ $Ala^{15}$ $Leu^{27}$ $Ser^{28}$ $Hse^{30}$ bGRF(1–30)NH—$C_2H_5$, $Val^2$ $Ser^8$ $Ala^{15}$ $Leu^{27}$ $Ser^{28}$ $Hse^{33}$ bGRF(1–33)$NH_2$, $Val^2$ $Ser^8$ $Ala^{15}$ $Leu^{27}$ $Ser^{28}$ $Hse^{33}$ bGRF(1–33)NH—$C_2H_5$, $Ile^2$ $Ser^8$ $Ala^{15}$ $Leu^{27}$ $Ser^{28}$ $Hse^{33}$ bGRF(1–33)$NH_2$, $Ile^2$ $Ser^8$ $Ala^{15}$ $Leu^{27}$ $Ser^{28}$ $Hse^{33}$ bGRF(1–33)NH—$C_2H_5$, or a non-toxic salt thereof.

Another embodiment of this invention is the peptide N-α-iPr-$Tyr^1$ $Thr^2$ N-ε-iPr-$Lys^{12,21}$ $Ala^{15}$ $Leu^{27}$ $Hse^{30}$ bGRF(1–30)$NH(C_2H_5)$ having the formula: N-α-iPr-Tyr-Thr-Asp-Ala-Ile-Phe-Thr-Asn-Ser-Tyr-Arg-N-ε-iPr-Lys-Val-Leu-Ala-Gln-Leu-Ser-Ala-Arg-N-ε-iPr-Lys-Leu-Leu-Gln-Asp-Ile-Leu-Ser-Arg-HseNH(Ethyl).

Another embodiment of this invention are GRF peptides where $R_{19}$ is Val or Ile, including the peptides $Thr^2$ $Ala^{15}$ $Val^{19}$ $Leu^{27}$ bGRF(1–29)$NH_2$ and $Thr^2$ $Ala^{15}$ $Ile^{19}$ $Leu^{27}$ bGRF(1–29)$NH_2$, preferably the peptides $Thr^2$ $Ser^8$ $Ala^{15}$ $Val^{19}$ $Leu^{27}$ $Ser^{28}$ $Hse^{30}$ bGRF(1–30)$NH_2$, $Thr^2$ $Ser^8$ $Ala^{15}$ $Val^{19}$ $Leu^{27}$ $Ser^{28}$ $Hse^{33}$ bGRF(1–33)$NH_2$, $Thr^2$ $Ser^8$ $Ala^{15}$ $Val^{19}$ $Leu^{27}$ $Ser^{28}$ $Hse^{37}$ bGRF(1–37)$NH_2$, $Thr^2$ $Ser^8$ $Ala^{15}$ $Val^9$ $Leu^{27}$ $Ser^{28}$ $Hse^{44}$ bGRF(1–44)$NH_2$, $Thr^2$ $Ser^8$ $Ala^{15}$ $Ile^{19}$ $Leu^{27}$ $Ser^{28}$ $Hse^{30}$ bGRF(1–30)$NH_2$, $Thr^2$ $Ser^8$ $Ala^{15}$ $Ile^{19}$ $Leu^{27}$ $Ser^{28}$ $Hse^{33}$ bGRF(1–33)$NH_2$, $Thr^2$ $Ser^8$ $Ala^{15}$ $Ile^{19}$ $Leu^{27}$ $Ser^{28}$ $Hse^{37}$ bGRF(1–37)$NH_2$, or $Thr^2$ $Ser^8$ $Ala^{15}$ $Ile^{19}$ $Leu^{27}$ $Ser^{28}$ $Hse^{44}$ bGRF(1–44)$NH_2$; more preferably $Ile^2$ $Ser^8$ $Ala^{15}$ $Val^{19}$ $Leu^{27}$ $Ser^{28}$ $Hse^{30}$ bGRF(1–30)$NH_2$, $Ile^2$ $Ser^8$ $Ala^{15}$ $Val^{19}$ $Leu^{27}$ $Ser^{28}$ $Hse^{33}$ bGRF(1–33)$NH_2$, $Ile^2$ $Ser^8$ $Ala^{15}$ $Val^{19}$ $Leu^{27}$ $Ser^{28}$$Hse^{37}$ bGRF(1–37)$NH_2$, $Ile^2$ $Ser^8$ $Ala^{15}$ $Val^{19}$ $Leu^{27}$ $Ser^{28}$ $Hse^{44}$ bGRF(1–44)$NH_2$, $Val^2$ $Ser^8$ $Ala^{15}$ $Val^{19}$ $Leu^{27}$ $Ser^{28}$ $Hse^{30}$ bGRF(1–30)$NH_2$, $Val^2$ $Ser^8$ $Ala^{15}$ $Val^{19}$ $Leu^{27}$ $Ser^{28}$ $Hse^{33}$ bGRF(1–33)$NH_2$, $Val^2$ $Ser^8$ $Ala^{15}$ $Val^{19}$ $Leu^{27}$ $Ser^{28}$ $Hse^{37}$ bGRF(1–37)$NH_2$, $Val^2$ $Ser^8$ $Ala^{15}$ $Val^{19}$ $Leu^{27}$ $Ser^{28}$ $Hse^{44}$ bGRF(1–44)$NH_2$, $Ile^2$ $Ser^8$ $Ala^{15}$ $Ile^{19}$ $Leu^{27}$ $Ser^{28}$ $Hse^{30}$ bGRF(1–30)$NH_2$, $Ile^2$ $Ser^8$ $Ala^{15}$ $Ile^{19}$ $Leu^{27}$ $Ser^{28}$ $Hse^{33}$ bGRF(1–33)$NH_2$, $Ile^2$ $Ser^8$ $Ala^{15}$ $Ile^{19}$ $Leu^{27}$ $Ser^{28}$ $Hse^{37}$ bGRF(1–37)$NH_2$, $Ile^2$ $Ser^8$ $Ala^{15}$ $Ile^{19}$ $Leu^{27}$ $Ser^{28}$ $Hse^{44}$ bGRF(1–44)$NH_2$, $Val^2$ $Ser^8$ $Ala^{15}$ $Ile^{19}$ $Leu^{27}$ $Ser^{28}$ $Hse^{30}$ bGRF(1–30)$NH_2$, $Val^2$ $Ser^8$ $Ala^{15}$ $Ile^{19}$ $Leu^{27}$ $Ser^{28}$ $Hse^{33}$ bGRF(1–33)$NH_2$, $Val^2$ $Ser^8$ $Ala^{15}$ $Ile^{19}$ $Leu^{27}$ $Ser^{28}$ $Hse^{37}$ bGRF(1–37)$NH_2$ or $Val^2$ $Ser^8$ $Ala^{15}$ $Ile^{19}$ $Leu^{27}$ $Ser^{28}$ $Hse^{44}$ bGRF(1–44)$NH_2$; or a non-toxic salt thereof.

Still another embodiment of this invention are N-terminally extended peptides, including for example N-α-(Tyr-Ser)-$Tyr^1$ $Thr^2$ $Ser^8$ $Ala^{15}$ $Leu^{27}$ $Ser^{28}$ bGRF(1–29) $NH_2$; N-α-(Tyr-Ser-Tyr-Thr)-$Tyr^1$ $Thr^2$ $Ser^8$ $Ala^{15}$ $Leu^{27}$ $Ser^{28}$ bGRF(1–29)$NH_2$; N-α-(Tyr-Thr)$_2$-$Tyr^1$ $Thr^2$ $Ser^8$ $Ala^{15}$ $Leu^{27}$ $Ser^{28}$ $Hse^{32}$ bGRF(1–32)$NH_2$; N-α-(Tyr-Ser)-$Tyr^1$ $Ile^2$ $Ser^8$ $Ala^{15}$ $Leu^{27}$ $Ser^{28}$ bGRF(1–29)$NH_2$; N-α-(Tyr-Ser-Tyr-Thr)-$Tyr^1$ $Ile^2$ $Ser^8$ $Ala^{15}$ $Leu^{27}$ $Ser^{28}$ bGRF (1–29)$NH_2$; N-α-(Asp-Ala-Tyr-Thr)-$Tyr^1$ $Ile^2$ $Ser^8$ $Ala^{15}$ $Leu^{27}$ $Ser^{28}$ bGRF(1–29)$NH_2$; N-α-(Asp-Ala)-$Tyr^1$ $Thr^2$ $Ser^8$ $Ala^{15}$ $Leu^{27}$ $Ser^{28}$ bGRF(1–37)$NH_2$; N-α-(Tyr-Thr)$_2$-$Tyr^1$ $Ile^2$ $Ser^8$ $Ala^{15}$ $Leu^{27}$ $Hse^{32}$ bGRF(1–32)$NH_2$; N-α-(Tyr-Ser)-$Tyr^1$ $Val^2$ $Ser^8$ $Ala^{15}$ $Leu^{27}$ $Ser^{28}$ bGRF (1–29)NH$_2$; N-α-(Tyr-Ser-Tyr-Thr)-Tyr$^1$ Val$^2$ Ser$^8$ Ala$^{15}$ Leu$^{27}$ Ser$^{28}$ bGRF(1–29)NH$_2$; N-α-(Tyr-Thr)$_2$-Tyr$^1$ Val$^2$ Ser$^8$ Ala$^{15}$ Leu$^{27}$ Ser$^{28}$ bGRF(1–29)NH$_2$; N-α-(Asp-Ala)-Tyr$^1$ Ile$^2$ Ser$^8$ Ala$^{15}$ Leu$^{27}$ Ser$^{28}$ bGRF(1–37)NH$_2$.

Another embodiment of this invention is any of the foregoing embodiments wherein Cya is substituted for Asp in position 3 and/or 25, preferably in position 3.

Evidence of the improved metabolic stability of the compounds of this invention (when compared to native GRF) is illustrated in Table I by the in vitro stability data provided. It is noteworthy that in bovine plasma in vitro, the analogs having Thr$^2$, Val$^2$, Ile$^2$ or Leu$^2$ were not cleaved after residue 2 by plasma DPP-IV under the experimental conditions used in the study (one hour plasma incubation). However, on extended plasma incubation, Thr$^2$ Ala$^{15}$ Leu$^{27}$ bGRF(1–29)NH$_2$ exhibited slight DPP-IV related cleavage.

In addition, the enhanced in vivo potency of the compounds of this invention is illustrated in Table I. For example, a person skilled in the art would recognize from the relative in vivo potency (at a dose of 0.01 nmol/kg) that Ile$^2$ Ala$^{15}$ Leu$^{27}$ bGRF(1–29)NH$_2$, trifluoroacetate salt would be expected to exhibit a potency of 10–20 times that of its isomer Leu$^2$ Ala$^{15}$ Leu$^{27}$ bGRF(1–29)NH$_2$, trifluoroacetate salt when the ED$_{50}$ of each is determined and compared.

The enhanced in vivo potency of the compounds of this invention where R$_{19}$ is Val or Ile is illustrated in FIGS. 1 and 2. For example, a person skilled in the art would recognize from the relative in vivo potency (at a dose of 0.01 nmol/kg) that Thr$^2$ Ala$^{15}$ Val$^{19}$ Leu$^{27}$ bGRF (1–29)NH$_2$, trifluoroacetate salt and Thr$^2$ Ala$^{15}$ Ile$^{19}$ Leu$^{27}$ bGRF (1–29)NH$_2$, trifluoroacetate salt are more bioactive than the native GRF.

For purposes of commercial production methodology, the carboxy terminal residue is preferably homoserine, homoserine lactone, homoserine amide, or a C$_1$–C$_8$ alkyl (preferably C$_1$–C$_4$ alkyl), secondary or tertiary amides of homoserine.

The synthetic GRF peptide analogs are synthesized by a suitable method, including for example the methods disclosed in U.S. Pat. No. 4,529,595 (Col 2, ln 35 to Col 5, ln 64) and U.S. Pat. No. 4,689,318 (Col 2, ln 23 to Col 9, ln 13), each of which are incorporated herein by reference.

Procedure A sets forth a method for synthesizing GRF peptide analogs of the subject invention.

Procedure A

The peptides are synthesized by solid-phase methodology utilizing an Applied Biosystems 430A peptide synthesizer (Applied Biosystems, Foster City, Calif.) and synthesis cycles supplied by Applied Biosystems. Boc Amino acids and other reagents were supplied by Applied Biosystems and other commercial sources. Sequential Boc chemistry using double couple protocols are applied to the starting p-methyl benzhydryl amine resin for the production of C terminal carboxamides. For the production of C terminal acids, the corresponding PAM resin is used. Asparagine, glutamine, and arginine are coupled using preformed hydroxy benztriazole esters. All other amino acids are coupled using the preformed symmetrical Boc amino acid anhydrides.

The following side chain protection is used:

Arg, Tosyl
Asp, Benzyl
Cys, 4-Methyl Benzyl
Glu, Benzyl
Ser, Benzyl
Thr, Benzyl
Tyr, 4-Bromo Carbobenzoxy
Lys, 2-Chloro Carbobenzoxy Boc deprotection is accomplished with trifluoroacetic acid (TFA) in methylene chloride. When Hse containing analogs are desired, Met should be incorporated by solid phase and then modified with cyanogen bromide after HF cleavage by methods well known in the art. This cyanogen bromide cleavage converts the Met to the C-terminal Hse lactone peptide. This can be converted to the Hse amide peptide by treatment with the appropriate amine in a solvent such as methanol or dimethyl formamide. Following completion of the synthesis, the peptides are deprotected and cleaved from the resin with anhydrous hydrogen fluoride containing 10% p-cresol. Cleavage of the side chain protecting group(s) and of the peptide from the resin is carried out at 0° C. or below, preferably –20° C. for thirty minutes followed by thirty minutes at 0° C. After removal of the HF, the peptide/resin is washed with ether, and the peptide extracted with glacial acetic acid and lyophilized. Before purification, crude cysteine containing peptides are then oxidized to the corresponding cysteic acid containing compound using performic acid at –10° C. to 10° C., preferably at 0° C., as described by Stewart et al., Solid Phase Peptide Synthesis, pg. 113, Pierce Chemical Company, Rockford, Ill., 1984. Conversion to C-terminal Hse lactones and Hse amides is carried out as described above.

Purification is carried out by ion exchange chromatography on a Synchroprep S-300 (SynChrom Inc. Linden, Ind.) cation exchange column. The peptide is applied using a buffer of 20 millimolar TRIS (pH 6.8) in 20% acetonitrile and eluted using a gradient of 0–0.3 molar sodium chloride in the same solvent. Compounds are further purified and desalted by reverse phase liquid chromatography on a Vydac C-18 (Separations Group, Hesperia, Calif.) column using water:acetonitrile gradients, each phase containing 0.1% TFA. The desired fractions are pooled and lyophilized yielding the desired GRF PEPTIDE as its trifluoroacetate salt. The trifluoroacetate salt can be converted, if desired to other suitable salts, by well known ion exchange methods.

Peptides are hydrolyzed under vacuum by a vapor phase method in a Pico-Tag Work Station (Waters) using constant boiling HCl (Pierce) in the presence of phenol as scavenger at 110 C. for 24 hrs. Hydrolysates are analyzed on a Beckman Amino Acid Analyzer, Model 6300. Peptide content is calculated using norleucine at a known concentration as an internal standard.

EXAMPLES

Example 1

Preparation of Thr$^2$ Ala$^{15}$ Leu$^{27}$ bGRF(1–29)NH$_2$, trifluoroacetate salt; Cpd. No. 1

The synthesis of the GRF analog peptide having the formula:

H-Tyr-Thr-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH2 (as the CF$_3$COOH salt) is conducted in a stepwise manner as in procedure A. Amino acid analysis, theoretical values in parentheses: Asp 3.96 (4); Thr 1.84 (2); Ser 1.79 (2); Glu 2.01 (2), Ala 3.04 (3); Val 0.99 (1), Ile 1.93 (2), Leu 5.05 (5); Tyr 1.96 (2); Phe 0.96 (1); Lys 2.02 (2); Arg 3.09 (3).

Example 2

Preparation of Val$^2$ Ala$^{15}$ Leu$^{27}$ bGRF(1–29)NH$_2$, trifluoroacetate salt; Cpd. No. 2

The synthesis of the GRF analog peptide having the formula:

H-Tyr-Val-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-

Leu-Asn-Arg-NH$_2$ (as the CF$_3$COOH salt) is conducted in a stepwise manner as in procedure A. Amino acid analysis, theoretical values in parentheses: Asp 4.11 (4); Thr 0.96 (1); Ser 1.79 (2); Glu 2.11 (2), Ala 3.04 (3); Val 2.1 (2), Ile 1.91 (2), Leu 5.17 (5); Tyr 2.00 (2); Phe 0.98 (1); Lys 1.99 (2); Arg 2.70 (3).

Example 3

Preparation of Ile$^2$ Ala$^{15}$ Leu$^{27}$ bGRF(1–29)NH$_2$, trifluoroacetate salt; Cpd. No. 3

The synthesis of the GRF analog peptide having the formula:
H-Tyr-Ile-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parentheses: Asp 4.12 (4); Thr 0.97 (1); Ser 1.75 (2); Glu 2.09 (2), Ala 3.00 (3); Val 1.05 (1), Ile 2.91 (3), Leu 5.16 (5); Tyr 2.00 (2); Phe 0.99 (1); Lys 1.98 (2); Arg 2.75 (3).

Example 4

Preparation of N-α-(Tyr-Thr)Tyr$^1$ Thr$^2$ Ala$^{15}$ Leu$^{27}$ bGRF (1–29)NH$_2$, trifluoroacetate salt; Cpd. No. 4

The synthesis of the GRF analog peptide having the formula Seq. ID NO 1:
H-Tyr-Thr-Tyr-Thr-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parentheses: Asp 4.05 (4); Thr 2.68 (3); Ser 1.77 (2); Glu 2.07 (2), Ala 2.90 (3); Val 1.08 (1), Ile 1.89 (2), Leu 5.20 (5); Tyr 2.87 (3); Phe 0.93 (1); Lys 2.01 (2); Arg 3.07 (3).

Example 5

Preparation of N-α-(Tyr-Thr)$_2$Tyr$^1$ Thr$^2$ Ala$^{15}$ Leu$^{27}$ bGRF (1–29)NH$_2$, trifluoroacetate salt; Cpd. No. 5

The synthesis of the GRF analog peptide having the formula Seq ID NO 2:
H-Tyr-Thr-Tyr-Thr-Tyr-Thr-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parentheses: Asp 4.06 (4); Thr 3.66 (4); Ser 1.85 (2); Glu 2.05 (2), Ala 2.93 (3); Val 1.09 (1), Ile 1.91 (2), Leu 5.15 (5); Tyr 3.91 (4); Phe 0.95 (1); Lys 2.00 (2); Arg 3.04 (3).

Example 6

Preparation of N-α-(Tyr-Thr)Tyr$^1$ Ala$^{15}$ Leu$^{27}$ bGRF(1–29) NH$_2$, trifluoroacetate salt; Cpd. No. 6

The synthesis of the GRF analog peptide having the formula Seq ID NO 3:
H-Tyr-Thr-Tyr-Ala-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parentheses: Asp 4.06 (4); Thr 1.86 (2); Ser 1.77 (2); Glu 2.07 (2), Ala 3.98 (4); Val 1.08 (1), Ile 1.89 (2), Leu 5.14 (5); Tyr 2.94 (3); Phe 0.96 (1); Lys 1.99 (2); Arg 3.04 (3).

Example 7

Preparation of N-α-(Tyr-Thr)Tyr$^1$ Ile$^2$ Ala$^{15}$ Leu$^{27}$ bGRF (1–29)NH$_2$, trifluoroacetate salt; Cpd. No. 7

The synthesis of the GRF analog peptide having the formula Seq ID NO 4:
H-Tyr-Thr-Tyr-Ile-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parentheses: Asp 4.07 (4); Thr 1.87 (2); Ser 1.75 (2); Glu 2.07 (2), Ala 2.94 (3); Val 1.09 (1), Ile 2.87 (3), Leu 5.12 (5); Tyr 2.92 (3); Phe 0.96 (1); Arg 3.05 (3).

Example 8

Preparation of N-α-(Tyr-Ser)Tyr$^1$ Thr$^2$ Ala$^{15}$ Leu$^{27}$ bGRF (1–29)NH$_2$, trifluoroacetate salt; Cpd. No. 8

The synthesis of the GRF analog peptide having the formula Seq ID NO 5:
H-Tyr-Ser-Tyr-Thr-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parentheses: Asp 4.11 (4); Thr 1.82 (2); Ser 2.64 (3); Glu 2.05 (2), Ala 2.90 (3); Val 1.04 (1), Ile 1.87 (2), Leu 5.16 (5); Tyr 2.92 (3); Phe 0.94 (1); Lys 2.01 (2); Arg 3.04 (3).

Example 9

Preparation of Val$^2$ Ser$^8$ Ala$^{15}$ Leu$^{27}$ Ser$^{28}$ Hse$^{45}$ bGRF (1–45)NH$_2$, trifluoroacetate salt Compound No. 9

The synthesis of the GRF analog peptide having the formula Seq ID NO 6:
H-Tyr-Val-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Gln-Gln-Gly-Glu-Arg-Asn-Gln-Glu-Gln-Gly-Ala-Lys-Val-Arg-Leu-Hse-NH$_2$ (as the CF$_3$COOH salt) is conducted in a stepwise manner as in procedure A. Amino acid analysis, theoretical values in parentheses: Asp 3.05 (3); Thr 0.93 (1); Ser 3.20 (4); Glu 8.41 (8); Gly 2.04 (2); Ala 4.17 (4); Val 2.87 (3); Ile 1.79 (2); Leu 5.96 (6); Tyr 1.88 (2); Phe 0.83 (1); Lys 2.94 (3); Arg 4.93 (5). Mass spectrum (M+H)$^+$, found 5179.3, theoretical 5179.9

Example 10

Preparation of Val$^2$ Ser$^8$ Ala$^{15}$ Leu$^{27}$ Ser$^{28}$ Hse$^{33}$ bGRF (1–33)NH$_2$, trifluoroacetate salt Compound No. 10

The synthesis of the GRF analog peptide having the formula Seq ID NO 7:
H-Tyr-Val-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Gln-Gln-Gly-Hse-NH$_2$ (as the CF$_3$COOH salt) is conducted in a stepwise manner as in procedure A. Amino acid analysis, theoretical values in parentheses: Asp 2.04 (2); Thr 0.93 (1); Ser 3.23 (4); Glu 4.19 (4); Gly 0.95 (1); Ala 3.21 (3); Val 1.93 (2); Ile 1.82 (2); Leu 4.96 (5); Tyr 1.91 (2); Phe 0.91 (1); Lys 1.99 (2); Arg 3.03 (3). Mass spectrum (M+H)$^+$, found 3770.1, theoretical 3770.4

Example 11

Preparation of Val$^2$ Ser$^8$ Ala$^{15}$ Leu$^{27}$ Ser$^{28}$ Hse$^{30}$ bGRF (1–30)NH$_2$, trifluoroacetate salt Compound No. 11

The synthesis of the GRF analog peptide having the formula Seq ID NO 8:
H-Tyr-Val-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Hse-NH$_2$ (as the CF$_3$COOH salt) is conducted in a stepwise manner as in procedure A. Amino acid analysis, theoretical values in parentheses: Asp 2.05 (2); Thr 0.96 (1); Ser 3.32 (4); Glu 2.04 (2); Ala 3.10 (3); Val 2.12 (2); Ile 1.86 (2); Leu 5.04 (5); Tyr 1.91 (2); Phe 0.89 (1); Lys 2.06 (2); Arg 3.05 (3). Mass spectrum (M+H)$^+$, found 3456.7, theoretical 3457.0

Example 12
Preparation of Val$^2$ Ser$^8$ Ala$^{15}$ Leu$^{27}$ Hse$^{28}$ bGRF(1-28)NH$_2$, trifluoroacetate salt Compound No. 12

The synthesis of the GRF analog peptide having the formula Seq ID NO 9:
H-Tyr-Val-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Hse-NH$_2$ (as the CF$_3$COOH salt) is conducted in a stepwise manner as in procedure A. Amino acid analysis, theoretical values in parentheses: Asp 2.05 (2); Thr 0.99 (1); Ser 2.46 (3); Glu 2.06 (2); Ala 3.09 (3); Val 2.02 (2); Ile 1.86 (2); Leu 5.01 (5); Tyr 1.96 (2); Phe 0.96 (1); Lys 2.00 (2); Arg 2.01 (2). Mass spectrum (M+H)$^+$, found 3213.5, theoretical 3213.8

Example 13
Preparation of Thr2 Ala$^{15}$ Val$^{19}$ Leu$^{27}$-bGRF(1-29)NH$_2$, trifluoroacetate salt Compound No. 13

The synthesis of the GRF analog peptide having the formula Seq ID NO 10:
H-Tyr-Thr-Asp-Ala-Ile-Phe-Thr-Asn-Ser-Tyr-Arg-Lys-Val-Leu-Ala-Gln-Leu-Ser-Val-Arg-Lys-Leu-Leu-Gln-Asp-Ile-Leu-Asn-Arg-NH$_2$ (as the CF$_3$COOH salt) is conducted in a stepwise manner as in procedure A. Amino acid analysis, theoretical values in parantheses: Asp 4.06 (4); Thr 1.57 (2); Ser 1.64 (2); Glu 2.10 (2); Ala 2.25 (2); Val 2.00 (2); Ile 1.68 (2); Leu 5.15 (5); Tyr 1.88 (2); Phe 0.94 (1); Lys 2.00 (2); Arg 2.94 (3).

Example 14
Preparation of Thr$^2$ Ala$^{15}$ Ile$^{19}$ Leu$^{27}$-bGRF(1-29)NH$_2$, trifluoroacetate salt Compound No. 14

The synthesis of the GRF analog peptide having the formula Seq ID NO 11:
H-Tyr-Thr-Asp-Ala-Ile-Phe-Thr-Asn-Ser-Tyr-Arg-Lys-Val-Leu-Ala-Gln-Leu-Ser-Ile-Arg-Lys-Leu-Leu-Gln-Asp-Ile-Leu-Asn-Arge-NH$_2$ (as the CF$_3$COOH salt) is conducted in a stepwise manner as in procedure A. Amino acid analysis, theoretical values in parantheses: Asp 4.09 (4); Thr 1.98 (2); Ser 1.64 (2); Glu 2.05 (2); Ala 2.25 (2); Val 1.0 (1); Ile 2.84 (3); Leu 5.07 (5); Tyr 1.87 (2); Phe 0.92 (1); Lys 1.97 (2); Arg 2.94 (3).

Example 15
Preparation of Thr$^2$ Ala$^{15}$ Leu$^{19}$ Leu$^{27}$-bGRF(1-29)NH$_2$, trifluoroacetate salt Compound No. 15

The synthesis of the GRF analog peptide having the formula Seq ID NO 12:
H-Tyr-Thr-Asp-Ala-Ile-Phe-Thr-Asn-Ser-Tyr-Arg-Lys-Val-Leu-Ala-Gln-Leu-Ser-Leu-Arg-Lys-Leu-Leu-Gln-Asp-Ile-Leu-Asn-Arge-NH$_2$ (as the CF$_3$COOH salt) is conducted in 50 a stepwise manner as in procedure A. Amino acid analysis, theoretical values in parantheses: Asp 4.08 (4); Thr 1.87 (2); Ser 1.72 (2); Glu 2.07 (2); Ala 1.93 (2); Val 1.04 (1); Ile 1.88 (2); Leu 6.11 (6); Tyr 1.90 (2); Phe 0.93 (1); Lys 2.03 (2); Arg 3.09 (3).

Following the stepwise manner as in procedure A, the following peptides can also be prepared:

Ile$^2$ Ser$^8$ Ile$^{15}$ Leu$^{27}$ Ser$^{28}$ bGRF(1-29)NH$_2$

Ile$^2$ Ser$^8$ Ala$^{15}$ Leu$^{27}$ Ser$^{28}$ Hse$^{30}$ bGRF(1-30)NH$_2$

Ile$^2$ Ser$^8$ Ala$^{15}$ Leu$^{27}$ Ser$^{28}$ Hse$^{30}$ bGRF(1-30)NH—C$_4$H$_9$

Ile$^2$ Ser$^8$ Ala$^{15}$ Leu$^{27}$ Ser$^{28}$ Hse$^{33}$ bGRF(1-33)NH—C$_2$H$_5$

Ile$^2$ Ser$^8$ Ala$^{15}$ Hse$^{27}$ bGRF(1-27)NH—C$_6$H$_{13}$

Thr$^2$ Ser$^8$ Ala$^{15}$ Leu$^{27}$ Ser$^{28}$ Hse$^{29}$ bGRF(1-29)NH—C$_8$H$_{17}$

Thr$^2$ Ser$^8$ Ala$^{15}$ Leu$^{27}$ Hse$^{28}$ bGRF(1-28)NH$_2$

Thr$^2$ Ser$^8$ Ala$^{15}$ Leu$^{27}$ Ser$^{28}$ Hse$^{33}$ bGRF(1-33)NH—C$_2$H$_5$

Thr$^2$ Ser$^8$ Ala$^{15}$ Leu$^{27}$ Ser$^{28}$ Hse$^{33}$ bGRF(1-33)NH$_2$

Thr$^2$ Val$^{15}$ bGRF(1-29)NH$_2$

Thr$^2$ Leu$^{15}$ Leu$^{27}$ bGRF(1-29)NH$_2$

Thr$^2$ Ile$^{15}$ Leu$^{27}$ bGRF(1-29)NH$_2$

Thr$^2$ Ser8 Val$^{15}$ Leu$^{27}$ Ser$^{28}$ Hse30 bGRF(1-30)NH$_2$

Thr$^2$ Ser$^8$ Ala$^{15}$ Ile$^{27}$ Ser$^{28}$ bGRF(1-29)NH$_2$

Thr$^2$ Ser$^8$ Leu$^{15}$ Leu$^{27}$ Ser$^{28}$ Hse30 bGRF(1-30)OH

Thr$^2$ Ser$^8$ Ile$^{15}$ Leu$^{27}$ Ser$^{28}$ bGRF(1-40)OH

Val$^2$ Ser$^8$ Val$^{15}$ Leu$^{27}$ Ser$^{28}$ bGRF(1-29)NH$_2$

Val$^2$ Ser$^8$ Ala$^{15}$ Ile$^{27}$ Ser$^{28}$ Hse37 bGRF(1-37)NH$_2$

Val$^2$ Ser$^8$ Leu$^{15}$ Leu$^{27}$ Ser$^{28}$ bGRF(1-29)NH$_2$

N-α-(Tyr-Thr)$_2$-Tyr$^1$ Thr$^2$ Val$^{15}$ Leu$^{27}$ bGRF(1-29)NH$_2$

N-α-(Tyr-Ser)-Tyr$^1$ Thr$^2$ Ala$^{15}$ Leu$^{27}$ Hse$^{30}$ bGRF(1-30)NH$_2$

N-α-(Tyr-Thr)$_2$-Tyr$^1$ Thr$^2$ Ile$^{15}$ Leu$^{27}$ bGRF(1-29)NH$_2$

N-α-(Tyr-Thr)-Tyr$^1$ Thr$^2$ Ser$^8$ Ala$^{15}$ Leu$^{27}$ Ser$^{28}$ bGRF(1-29)NH$_2$

N-α-(Tyr-Ser-Tyr-Thr)-Tyr$^1$ Thr$^2$ Ala$^{15}$ Leu$^{27}$ bGRF(1-29)NH$_2$

N-α-(Tyr-Thr-Tyr-Ser)-Tyr$^1$ Thr$^2$ Ala$^{15}$ Leu$^{27}$ bGRF(1-29)NH$_2$

N-α-(Asp-Ala)-Tyr$^1$ Thr$^2$ Ala$^{15}$ Leu$^{27}$ Hse$^{33}$ bGRF(1-33)NH—C2H$_5$

N-α-(Asp-Ala)-Tyr$^1$ Thr$^2$ Ser$^8$ Ala$^{15}$ Leu$^{27}$ Ser$^{28}$ Hse$^{30}$ bGRF(1-30)NH—C$_4$H$_9$

N-α-(Asp-Ala-Tyr-Thr)-Tyr$^1$ Thr$^2$ Ser$^8$ Ala$^{15}$ Leu$^{27}$ Ser$^{28}$ bGRF(1-29)NH$_2$

Thr$^2$ Cya$^3$ Ala$^{15}$ Leu$^{27}$ bGRF(1-29)NH$_2$

Thr$^2$ Cya$^3$ Ala$^{15}$ Ser$^8$ Leu$^{27}$ Ser$^{28}$ bGRF(1-29)NH$_2$

Val$^2$ Cya$^3$ Ala$^{15}$ Leu$^{27}$ bGRF(1-29)NH$_2$

Ile$^2$ Cya$^3$ Ala$^{15}$ Leu$^{27}$ bGRF(1-29)NH$_2$

Ile$^2$ Ser$^8$ Ala$^{15}$ Val$^{19}$ Leu$^{27}$ Ser$^{28}$ Hse$^{30}$ bGRF(1-30)NH$_2$

Ile$^2$ Ser$^8$ Ala$^{15}$ Val$^{19}$ Leu$^{27}$ Ser$^{28}$ Hse$^{33}$ bGRF(1-33)NH$_2$

Ile$^2$ Ser$^8$ Ala$^{15}$ Val$^{19}$ Leu$^{27}$ Ser$^{28}$ Hse$^{37}$ bGRF(1-37)NH$_2$

Ile$^2$ Ser$^8$ Ala$^{15}$ Val$^{19}$ Leu$^{27}$ Ser$^{28}$ Hse$^{44}$ bGRF(1-44)NH$_2$

Val$^2$ Ser$^8$ Ala$^{15}$ Val$^{19}$ Leu$^{27}$ Ser$^{28}$ Hse$^{30}$ bGRF(1-30)NH$_2$

Val$^2$ Ser$^8$ Ala$^{15}$ Val$^{19}$ Leu$^{27}$ Ser$^{28}$ Hse$^{33}$ bGRF(1-33)NH$_2$

Val$^2$ Ser$^8$ Ala$^{15}$ Val$^{19}$ Leu$^{27}$ Ser$^{28}$ Hse$^{37}$ bGRF(1-37)NH$_2$

Val$^2$ Ser$^8$ Ala$^{15}$ Val$^{19}$ Leu$^{27}$ Ser$^{28}$ Hse$^{44}$ bGRF(1-44)NH$_2$

Ile$^2$ Ser$^8$ Ala$^{15}$ Ile$^{19}$ Leu$^{27}$ Ser$^{28}$ Hse$^{30}$ bGRF(1-30)NH$_2$

Ile$^2$ Ser$^8$ Ala$^{15}$ Ile$^{19}$ Leu$^{27}$ Ser$^{28}$ Hse$^{33}$ bGRF(1-33)NH$_2$

Ile$^2$ Ser$^8$ Ala$^{15}$ Ile$^{19}$ Leu$^{27}$ Ser$^{28}$ Hse$^{37}$ bGRF(1-37)NH$_2$

Ile$^2$ Ser$^8$ Ala$^{15}$ Ile$^{19}$ Leu$^{27}$ Ser$^{28}$ Hse$^{44}$ bGRF(1-44)NH$_2$

Val$^2$ Ser$^8$ Ala$^{15}$ Ile$^{19}$ Leu$^{27}$ Ser$^{28}$ Hse$^{30}$ bGRF(1-30)NH$_2$

Val$^2$ Ser$^8$ Ala$^{15}$ Ile$^{19}$ Leu$^{27}$ Ser$^{28}$ Hse$^{33}$ bGRF(1-33)NH$_2$

Val$^2$ Ser$^8$ Ala$^{15}$ Ile$^{19}$ Leu$^{27}$ Ser$^{28}$ Hse$^{37}$ bGRF(1-37)NH$_2$

Val$^2$ Ser$^8$ Ala$^{15}$ Ile$^{19}$ Leu$^{27}$ Ser$^{28}$ Hse$^{44}$ bGRF(1-44)NH$_2$

Thr$^2$ Ser$^8$ Ala$^{15}$ Val$^{19}$ Leu$^{27}$ Ser$^{28}$ Hse$^{30}$ bGRF(1-30)NH$_2$

Thr$^2$ Ser$^8$ Ala$^{15}$ Val$^{19}$ Leu$^{27}$ Ser$^{28}$ Hse$^{33}$ bGRF(1-33)NH$_2$

Thr$^2$ Ser$^8$ Ala$^{15}$ Val$^{19}$ Leu$^{27}$ Ser$^{28}$ Hse$^{37}$ bGRF(1-37)NH$_2$

Thr$^2$ Ser$^8$ Ala$^{15}$ Val$^{19}$ Leu$^{27}$ Ser$^{28}$ Hse$^{44}$ bGRF(1-44)NH$_2$

Thr$^2$ Ser$^8$ Ala$^{15}$ Ile$^{19}$ Leu$^{27}$ Ser$^{28}$ Hse$^{30}$ bGRF(1-30)NH$_2$

Thr$^2$ Ser$^8$ Ala$^{15}$ Ile$^{19}$ Leu$^{27}$ Ser$^{28}$ Hse$^{33}$ bGRF(1-33)NH$_2$

Thr$^2$ Ser$^8$ Ala$^{15}$ Ile$^{19}$ Leu$^{27}$ Ser$^{28}$ Hse$^{37}$ bGRF(1-37)NH$_2$

Thr$^2$ Ser$^8$ Ala$^{15}$ Ile$^{19}$ Leu$^{27}$ Ser$^{28}$ Hse$^{44}$ bGRF(1-44)NH$_2$

PROCEDURES

Procedure B

In addition to preparation of GRF analogs by solid phase methods, the analogs can be obtained by recombinant DNA methodology by the procedure described for Leu$^{27}$ bGRF (1–44)OH (European Patent Application 0212531) with the following modifications in the segment of DNA-coding for bGRF(1–44)OH the codons for Ala$^2$, Asn$^8$, Gly$^{15}$ and Asn$^{28}$ are replaced by the codons: for example (ACT) Thr$^2$ or (ATT) Ile$^2$ or (GTT) Val$^2$, (AGT) Ser$^8$, (GCT) Ala$^{15}$, (AGT) Ser$^{28}$, respectively.

Additionally, for Cya$^3$ containing GRF analogs, the codon GAT (Asp$^3$) is replaced by the codon TGT for Cys$^3$. After expression of the protein and cleavage with cyanogen bromide in formic acid as described in the above European Patent Application, hydrogen peroxide is added to the solution at about 0° C. to effect oxidation of the Cys residues to Cya. The peptide is then purified by the methods described.

Additionally, for N-terminally extended GRF analogs, the DNA segments coding for the extension are added to the N-terminus as follows: (TATACT) for Tyr-Thr, (TATACT)$_n$ for (Tyr-Thr)$_n$ or (TATAGT) for Tyr-Ser, (TATAGT)$_n$ for (Tyr-Ser)$_n$, or (TATAGTTATACT) for Tyr-Ser-Tyr-Thr or (TATACTTATAGT) for Tyr-Thr-Tyr-Ser, (GATGCT) for Asp-Ala etc. The gene for the precursor protein is inserted into an *E. coli* expression vector. After expression of the protein isolation of the inclusion bodies and then cleaving them with cyanogen bromide in formic acid as described in the above European Patent Application, the formic acid is removed under reduced pressure. The crude peptide is then purified by the methods described.

The ability to produce the compounds of the subject invention by known recombinant DNA technology is possible since the claimed peptides are constituted entirely of naturally occurring amino acids. This is in contrast to known analogs which contain non-DNA-coded components, such as D-Ala and/or desaminoTyr, and will require for any large scale production a costly chemical synthesis or a combination of genetic engineering with chemical procedures.

Recombinant host microorganisms used in this invention are made by recombinant DNA techniques well known to those skilled in the art and set forth, for example, in Molecular Cloning, T. Maniatis, et al., Cold Spring Harbor Laboratory, (1982) and B. Perbal, A Practical Guide to Molecular Cloning, John Wiley & Sons (1984), which are incorporated herein by reference.

C-terminal Hse(lactone), HseOH and HseN(R$_a$)(R$_b$) analogs can be prepared by the methods disclosed in Kempe et al, BIO/TECHNOLOGY, Vol 4, pp 565–568 (1986).

Procedure C

This procedure deals with the preparation of N-alkylated GRF analogs described in the subject invention. The peptides will be made using either chemical or biotechnology procedures (Procedure A or Procedure B, respectively). N-alkylation will then be achieved by known methods e.g. Murphy, W. A. and Coy, D. H., Potent long-acting alkylated analogs of growth hormone-releasing factor, Peptide Research 1, 36–41 (1988). V. Sythyamoorthy et al. Reductive methylation of botulinum neurotoxin types A and B. Mol. Cell. Biochem. 83, 65–72 (1988).

Following Procedure C, the following peptides can also be prepared:

N-ε-iPr-Tyr$^1$ Thr$^2$ Ser$^8$ N-ε-iPr-Lys$^{12,21}$ Val$^{15}$ Leu$^{27}$ Ser$^{28}$bGRF(1–29)NH$_2$

N-ε-iPr-Tyr$^1$ Thr$^2$ Ser$^8$ N-ε-iPr-Lys$^{12,21}$ Ala$^{15}$ Leu$^{27}$ bGRF(1–40)NH$_2$

N-ε-Bzl-Tyr$^1$ Thr$^2$ Ser$^8$ N-ε-Bzl-Lys$^{12,21}$ Val$^{15}$ Ile$^{27}$ Ser$^{28}$ bGRF(1–32)NH$_2$

N-ε-iPr-Tyr$^1$ Ile$^2$ Ser$^8$ N-ε-iPr-Lys$^{12,21}$ Ala$^{15}$ Leu$^{27}$ bGRF (1–40)NH$_2$

N-ε-Bzl-Tyr$^1$ Val$^2$ Ser$^8$ N-ε-Bzl-Lys$^{12,21}$ Val$^{15}$ Ile$^{27}$ Ser$^{28}$ bGRF(1–32)NH$_2$

All of the synthetic GRF peptides of the subject invention, including the peptides prepared in the Examples, are considered to be biologically active and useful for stimulating the release of GH by the pituitary.

Dosages between about 10 nanograms and about 5 micrograms of these peptides per kilogram (kg) of body weight are considered to be particulary effective in causing GH secretion.

Stimulation of GH secretion by such peptides should result in an attendant increase in growth for humans, bovine and other animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals such as chickens, turkeys, pigs, goats, cattle and sheep, and may be used in agriculture for raising fish and other cold-blooded marine animals, e.g., sea turtles and eels, and amphibians, to accelerate growth and increase the ratio of protein to fat gained by feeding effective amounts of the peptides. These analogs may be used for stimulation of the immune functions in human and animal for the treatment of diabetes resulting from abnormalities in growth hormone production or for the improvement of bone, wound or burn healing, or osteoporosis. These analogs may be used to enhance hair growth.

Daily dosages of between 10 nanograms/Kg and about 50 micro-grams/Kg body weight are considered to be particularly effective in increasing lactation, growth and stimulating the immune functions.

For administration to humans and animals, these synthetic peptides should have purity of at least about 93% and preferably at least 98%.

These synthetic peptides or the nontoxic salts thereof, combined with a pharmaceutically or veterinarily acceptable carrier to form a pharmaceutical composition, preferably as sustained release formulations, may be administered to animals, including humans, either intravenously, subcutaneously, intramuscularly, percutaneously, e.g. intranasally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to administered by intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parental dosage will be from about 100 nanograms to about 50 micrograms of the peptide per kilogram of the body weight of the host.

Although the invention has been described with regard to its preferred embodiments, it should be understood that various changes and modifications as would be obvious to one having the ordinary skill in this art may be made without departing from the scope of the invention which is set forth in the claims appended hereto. For example, modifications in the peptide chain, particularly deletions of one or two residues beginning at the C-terminus of the peptide, can be made in accordance with known experimental practices to date to create peptides that retain very substantial portions of the biological potency of the peptide, and such peptides are considered as being within the scope of the invention. Moreover, additions may be made to the C-terminus, and/or to the N-terminus, and/or generally equivalent residues can be substituted for naturally occurring residues, as is known in the overall art of peptide chemistry, to produce other analogs, having increased resistance to proteolysis, for example, and also having at least a substantial portion of the potency of the claimed polypeptide, without deviating from the scope of the invention, such as those illustrated by Compounds 1–15. Likewise known substitutions in the carboxyl moiety at the C-terminus, e.g. a lower alkyl amide, also produce equivalent molecules.

In the same manner as disclosed herein,

GRF PEPTIDES of the formula R'-$R_1$-R'$_2$-$R_3$-Ala-Ile-Phe-Thr-$R_8$-Ser-Tyr-Arg-R'$_{12}$-$R_{13}$-Leu-$R_{15}$-Gln-Leu-$R_{18}$-$R_{19}$-Arg-R'$_{21}$-$R_{22}$-Leu-Gln-$R_{25}$-Ile-$R_{27}$-$R_{28}$-Arg-Gln-Gln-Gly-Glu-$R_{34}$-$R_{35}$-Gln-Glu-$R_{38}$-$R_{39}$-$R_{40}$-Arg-$R_{42}$-Arg-Leu-Z wherein R' is H—$(Y—X)_n$ or H—$(Y—X)_m(Y'—X')_p$ wherein Y and Y', being the same or different, is a naturally occurring amino acid; X and X', being the same or different, is selected from Thr or Ser, or when Y or Y' is Asp, then X and X' is Ala; n is 1–10; m is 1–5; p is 1–5;

$R_1$ is Tyr or His;

R'$_2$ is Ala, D-Ala, Thr, Val or Ile;

$R_3$ is Asp, Glu or Cya;

$R_8$ is Asn or Ser;

R'$_{12}$ is Lys or Arg;

$R_{13}$ is Val or Ile;

$R_{15}$ is Ala, Val, Leu, Ile or Gly;

$R_{18}$ is Ser or Tyr;

$R_{19}$ is Ala, Val, Ile;

R'$_{21}$ is Lys or Arg;

$R_{22}$ is Ala or Leu;

$R_{25}$ is Asp, Glu or Cya;

$R_{27}$ is Met, Ile or Leu;

$R_{28}$ is Asn or Ser;

$R_{34}$ is Ser or Arg;

$R_{35}$ is Asn or Ser;

$R_{38}$ is Arg or Gln;

$R_{39}$ is Gly or Arg;

$R_{40}$ is Ala or Ser;

$R_{42}$ is Ala, Val or Phe; and

Z signifies the carboxyl moiety of the amino acid residue at the C-terminal and is the radical —$COOR_a$, —$CR_aO$, —$CONHNHR_a$, —$CON(R_a)(R_b)$ or —$CH_2OR_a$, with $R_a$ and $R_b$ being $C_1$–$C_8$ alkyl or hydrogen; or a biologically active fragment thereof extending from R at the N-terminus to a residue in any of positions 27 through 44 as its C-terminus; or a Hse(lactone), HseOH or HseN($R_a$)($R_b$) of the foregoing and/or a non-toxic salt of the foregoing; can be made in accordance with known experimental practices to date to create peptides that retain very substantial portions of the biological potency of the peptide, and such peptides are considered as also being another aspect of the invention disclosed herein. These peptides can be prepared (substituting N-Methyl-D-Ala, D-Ala or preferably Ala at the 2 position for Val, Ile or Thr) and can be utilized in the same general manner.

TABLE I

In vitro stability in bovine plasma and in vivo bioactivity in steer of GRF analogs substituted at position 2 and 15.

| Compound[+] | In vitro stability[*] (% Inact peptide after 1 hr) | In vivo relative potency iv[#] | sc[$] |
|---|---|---|---|
| STUDY I | | | |
| bGRF(1–14)$NH_2$ | nd | 100[a] | |
| Leu$^{27}$-bGRF(1–29)$NH_2$ | 39.8* | 106[a] | |
| Ala$^{15}$,Leu$^{27}$-bGRF(1–29)$NH_2$ | 56.2* | 118[a] | |
| Thr$^2$,Leu$^{27}$-bGRF(1–29)$NH_2$++ | 75.6* | 94[a] | |
| Thr$^2$,Ala$^{15}$,Leu$^{27}$-bGRF(1–29)$NH_2$++ | 91.1* | 195[b] | |
| STUDY II | | | |
| bGRF(1–44)$NH_2$ | nd | 100[a] | 100[a] |
| Leu$^{27}$-bGRF(1–29)$NH_2$ | 46.8** | nd | nd |
| Leu$^2$,Ala$^{15}$,Leu$^{27}$-bGRF(1–29)$NH_2$++ | 86.3** | 100[a] | nd |
| Val$^2$,Ala$^{15}$,Leu$^{27}$-bGRF(1–29)$NH_2$++ | 83.4** | 167[b] | 214[b] |
| Ile$^2$,Ala$^{15}$,Leu$^{27}$-bGRF(1–29)$NH_2$++ | 80.3** | 171[b] | 16c[c] |
| Thr$^2$,Ala$^{15}$,Leu$^{27}$-bGRF(1–29)$NH_2$++ | nd | 148[b] | 187[b] |

[*]Peptides at 0.03 mM were incubated with bovine plasma at 37° C. for one hr. Aliquots of 0.1 ml were quenched with 2 ml of 0.2% aqueous trifluoroacetic acid solution and subjected to solid phase extraction and HPLC analysis as described in T.M. Kubiak et al. Drug Met. Disp. 17, 393–397 (1989).
[#]Steers were injected iv with peptides at the dose of 0.01 nmol/kg and the procedures were as described in W.M. Moseley et al. J. Endocr. 117, 253–259 (1988). Relative potency was calculated on the basis of the area under serum growth hormone (GH) curve monitored for 2 hrs after treatment.
[$]Steers were injected subcutaneously with peptides at the dose of 0.75 nmol/kg. Relative potency was calculated on the basis of the area under serum GH curve monitored for 6 hrs after treatment.
[a,b,c]values with different superscripts within each column and/or study were statistically different at p < 0.05.
nd = not determined
*Plasma pool 1
**Plasma pool 2, different from 1
+ as the trifluoroacetate salt
++ No cleavage after residue 2 was observed upon incubation in bovine plasma in vitro over a 1 hr incubation period.

Figure 1:
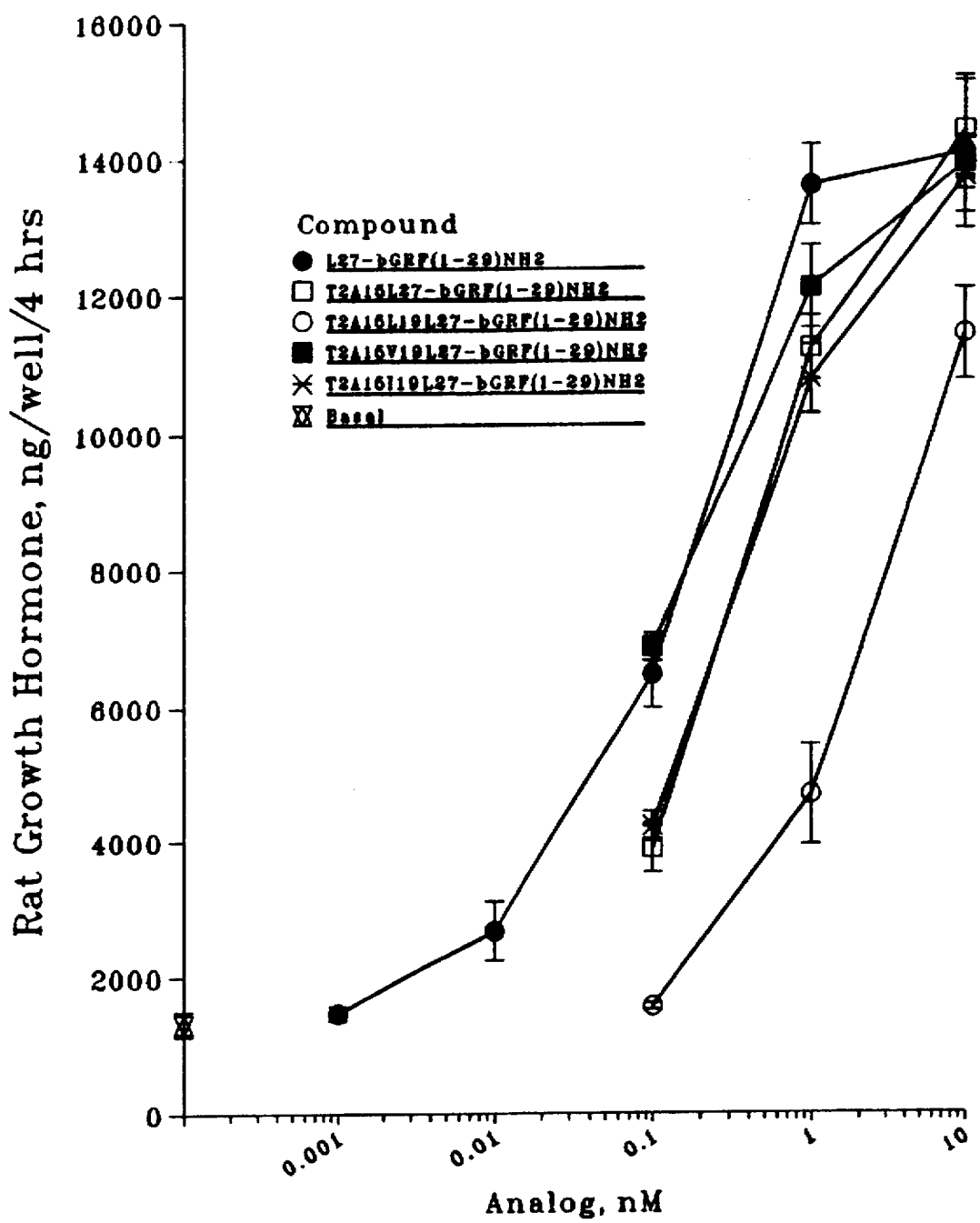
FIG. 1.
Figure 2:
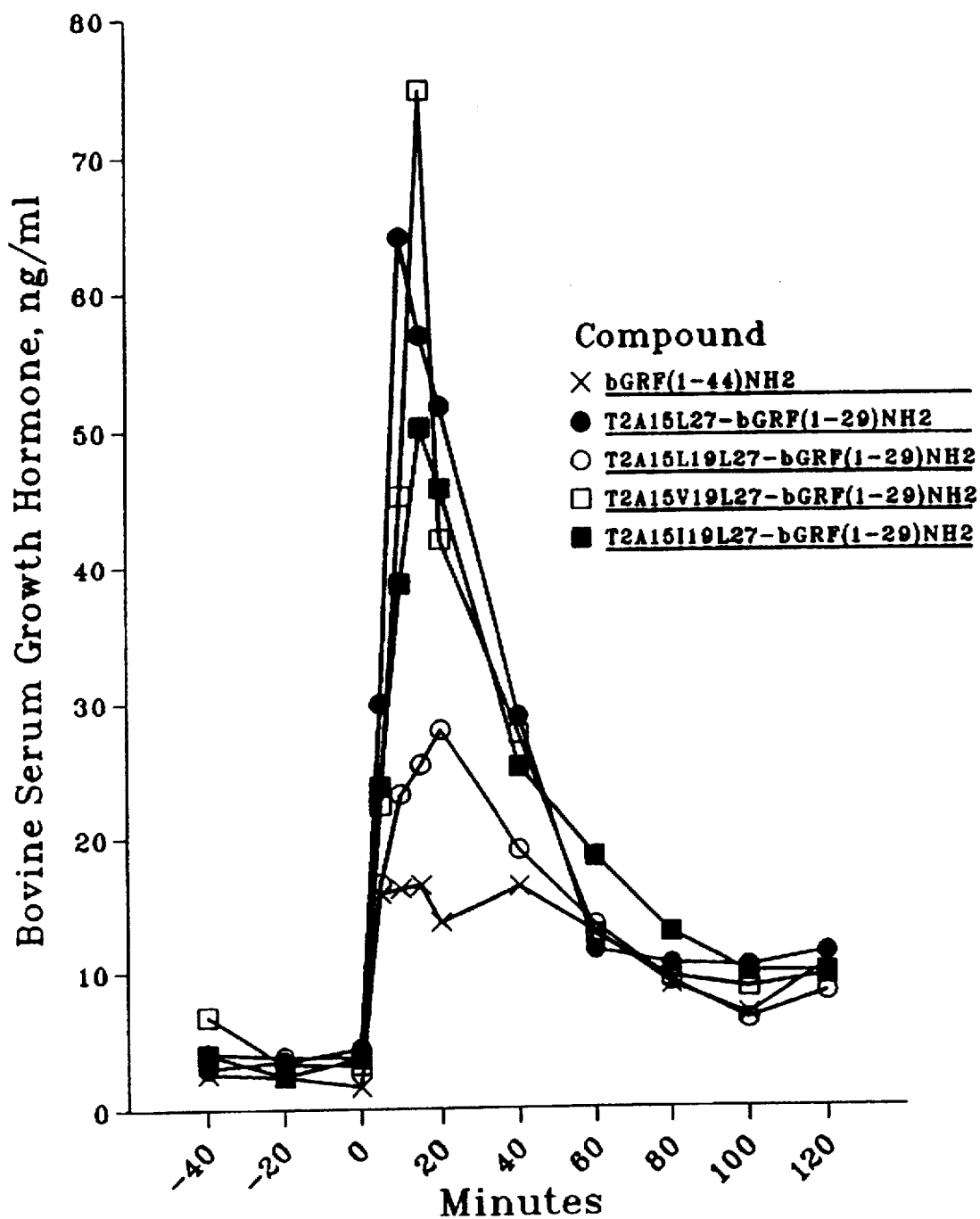

Effect of analogs of Thr$^2$, Ala$^{15}$, Leu$^{27}$-bGRF(1–29)$NH_2$ on growth hormone (GH) release in rat pituitary cell cultures in vitro. The assay was performed according to procedure of Frohman and Downs, Methods Enzymol. 124, 371–389 (1986). Note that the Leu$^{19}$ substitution was deleterious to the analog GH-releasing potency while Val$^{19}$ and Ile$^{19}$ modifications resulted in analogs with respectively increased or unchanged bioactivity in vitro as compared with Thr$^2$, Ala$^{15}$, Leu$^{27}$-bGRF(1–29)$NH_2$. Leu$^{27}$-bGRF(1–29)$NH_2$ was used as the assay standard.

FIG. 2.

Mean concentration of serum growth hormone (GH) in meal-fed Holstein steers after intravenous injection (10 pmol/kg) of GRF analogs. The assay was performed as described by Moseley et al., J. Endocrinol. 117, 252-259 (1988). Bovine GRF(1-44)NH$_2$ was used as the assay standard.

We claim:

1. A GRF PEPTIDE having Thr, Val or Ile residue in place of the amino acid residue normally found at position 2 and having an amino acid selected from the group consisting of Ala, Val, Leu and Ile or Gly at position 15.

2. A GRF PEPTIDE of claim 1 wherein the amino acid at position 15 is Ala.

3. A GRF PEPTIDE of claim 1 having the formula
R-$R_1$-$R_2$-$R_3$-Ala-Ile-Phe-Thr-$R_8$-Ser-Tyr-Arg-$R_{12}$-$R_{13}$-Leu-$R_{15}$-Gln-Leu-$R_{18}$-$R_{19}$-Arg-$R_{21}$-$R_{22}$-Leu-Gln-$R_{25}$-Ile-$R_{27}$-$R_{28}$-Arg-Gln-Gln-Gly-Glu-$R_{34}$-$R_{35}$-Gln-Glu-$R_{38}$-$R_{39}$-$R_{40}$-Arg-$R_{42}$-Arg-Leu-Z
wherein R is H, $C_1$–$C_5$ alkyl or benzyl;

$R_1$ is Tyr or His;

$R_2$ is Thr, Val or Ile;

$R_3$ is Asp, Glu or Cya;

$R_8$ is Asn or Ser;

$R_{12}$ is Lys or Arg, or N-ε-alkyl- or N-ε-benzyl-Lys when R is $C_1$–$C_5$ alkyl or benzyl;

$R_{13}$ is Val or Ile;

$R_{15}$ is Ala, Val, Leu or Ile;

$R_{18}$ is Ser or Tyr;

$R_{19}$ is Ala, Val or Ile;

$R_{21}$ is Lys or Arg, or N-ε-alkyl- or N-ε-benzyl-Lys when R is $C_1$–$C_5$ alkyl or benzyl;

$R_{22}$ is Ala or Leu;

$R_{25}$ is Asp or Glu;

$R_{27}$ is Met, Ile or Leu;

$R_{28}$, is Asn or Ser;

$R_{34}$ is Ser or Arg;

$R_{35}$ is Asn or Ser;

$R_{38}$ is Arg or Gln;

$R_{39}$ is Gly or Arg;

$R_{40}$ is Ala or Ser;

$R_{42}$ is Ala, Val or Phe; and

Z signifies the carboxyl moiety of the amino acid residue at the C-terminal and is the radical —$COOR_a$, —$CR_aO$, —$CONHNHR_a$, —$CON(R_a)(R_b)$ or —$CH_2OR_a$, with $R_a$ and $R_b$ being $C_1$–$C_8$ alkyl or hydrogen; or a biologically active fragment thereof extending from R at the N-terminus to a residue in any of positions 27 through 44 as its C-terminus; or a Hse(lactone), HseOH or HseN($R_a$)($R_b$) of the foregoing and/or a non-toxic salt of the foregoing.

4. A GRF PEPTIDE of claim 3 wherein $R_{19}$ is Val or Ile.

5. A GRF PEPTIDE according to claim 4 selected from the group consisting of $Thr^2$ $Ala^{15}$ $Val^{19}$ $Leu^{27}$ bGRF(1–29)$NH_2$, $Thr^2$ $Ala^{15}$ $Ile^{19}$ $Leu^{27}$ bGRF(1–29)$NH_2$, $Thr^2$ $Ser^8$ $Ala^{15}$ $Val^{19}$ $Leu^{27}$ $Ser^{28}$ $Hse^{30}$ bGRF(1–30)$NH_2$, $Thr^2$ $Ser^8$ $Ala^{15}$ $Val^{19}$ $Leu^{27}$ $Ser^{28}$ $Hse^{33}$ bGRF(1–33)$NH_2$, $Thr^2$ $Ser^8$ $Ala^{15}$ $Val^{19}$ $Leu^{27}$ $Ser^{28}$ $Hse^{37}$ bGRF(1–37)$NH_2$, $Thr^2$ $Ser^8$ $Ala^{15}$ $Val^{19}$ $Leu^{27}$ $Ser^{28}$ $Hse^{44}$ bGRF(1–44)$NH_2$, $Thr^2$ $Ser^8$ $Ala^{15}$ $Ile^{19}$ $Leu^{27}$ $Ser^{28}$ $Hse^{30}$ bGRF(1–30)$NH_2$, $Thr^2$ $Ser^8$ $Ala^{15}$ $Ile^{19}$ $Leu^{27}$ $Ser^{28}$ $Hse^{33}$ bGRF(1–33)$NH_2$, $Thr^2$ $Ser^8$ $Ala^{15}$ $Ile^{19}$ $Leu^{27}$ $Ser^{28}$ $Hse^{37}$ bGRF(1–37)$NH_2$, $Thr^2$ $Ser^8$ $Ala^{15}$ $Ile^{19}$ $Leu^{27}$ $Ser^{28}$ $Hse^{44}$ bGRF(1–44)$NH_2$, $Ile^2$ $Ser^8$ $Ala^{15}$ $Val^{19}$ $Leu^{27}$ $Ser^{28}$ $Hse^{30}$ bGRF(1–30)$NH_2$, $Ile^2$ $Ser^8$ $Ala^{15}$ $Val^{19}$ $Leu^{27}$ $Ser^{28}$ $Hse^{33}$ bGRF(1–33)$NH_2$, $Ile^2$ $Ser^8$ $Ala^{15}$ $Val^{19}$ $Leu^{27}$ $Ser^{28}$ $Hse^{37}$ bGRF(1–37)$NH_2$, $Ile^2$ $Ser^8$ $Ala^{15}$ $Val^{19}$ $Leu^{27}$ $Ser^{28}$ $Hse^{44}$ bGRF(1–44)$NH_2$, $Val^2$ $Ser^8$ $Ala^{15}$ $Val^{19}$ $Leu^{27}$ $Ser^{28}$ $Hse^{30}$ bGRF(1–30)$NH_2$, $Val^2$ $Ser^8$ $Ala^{15}$ $Val^{19}$ $Leu^{27}$ $Ser^{28}$ $Hse^{33}$ bGRF(1–33)$NH_2$, $Val^2$ $Ser^8$ $Ala^{15}$ $Val^{19}$ $Leu^{27}$ $Ser^{28}$ $Hse^{37}$ bGRF(1–37)$NH_2$, $Val^2$ $Ser^8$ $Ala^{15}$ $Val^{19}$ $Leu^{27}$ $Ser^{28}$ $Hse^{44}$ bGRF(1–44)$NH_2$, $Ile^2$ $Ser^8$ $Ala^{15}$ $Ile^{19}$ $Leu^{27}$ $Ser^{28}$ $Hse^{30}$ bGRF(1–30)$NH_2$, $Ile^2$ $Ser^8$ $Ala^{15}$ $Ile^{19}$ $Leu^{27}$ $Ser^{28}$ $Hse^{33}$ bGRF(1–33)$NH_2$, $Ile^2$ $Ser^8$ $Ala^{15}$ $Ile^{19}$ $Leu^{27}$ $Ser^{28}$ $Hse^{37}$ bGRF(1–37)$NH_2$, $Val^2$ $Ser^8$ $Ala^{15}$ $Ile^{19}$ $Leu^{27}$ $Ser^{28}$ $Hse^{44}$ bGRF(1–44)$NH_2$, $Val^2$ $Ser^8$ $Ala^{15}$ $Ile^{19}$ $Leu^{27}$ $Ser^{28}$ $Hse^{30}$ bGRF(1–30)$NH_2$, $Val^2$ $Ser^8$ $Ala^{15}$ $Ile^{19}$ $Leu^{27}$ $Ser^{28}$ $Hse^{33}$ bGRF(1–33)$NH_2$, $Val^2$ $Ser^8$ $Ala^{15}$ $Ile^{19}$ $Leu^{27}$ $Ser^{28}$ Hse37 bGRF(1–37)$NH_2$ and $Val^2$ $Ser^8$ $Ala^{15}$ $Ile^9$ $Leu^{27}$ $Ser^{28}$ $Hse^{44}$ bGRF(1–44)$NH_2$; or a non-toxic salt thereof.

6. A GRF PEPTIDE of claim 3 wherein R is H and $R_{15}$ is Ala.

7. A GRF PEPTIDE of claim 1 wherein $R_1$ is Tyr.

8. A GRF PEPTIDE of claim 7 wherein $R_8$ and $R_{28}$ are Ser.

9. A GRF PEPTIDE of claim 8 having the formula H-Tyr-Val-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Gln-Gln-Gly-Hse-$NH_2$ or a non-toxic salt thereof.

10. A GRF PEPTIDE of claim 3 wherein $R_2$ is Thr.

11. A GRF PEPTIDE of claim 10 having the formula H-Tyr-Thr-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Gln-Gln-Gly-Hse-$NH_2$, H-Tyr-Thr-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Gln-Gln-Gly-Hse-$NH$-$C_2H_5$, H-Tyr-Thr-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Hse-$NH_2$, or a non-toxic salt thereof.

12. A GRF PEPTIDE of claim 3 wherein $R_2$ is Ile.

13. A GRF PEPTIDE of claim 12 having the formula H-Tyr-Ile-Asp-Ala-Ile-Phe-Thr-Ser-Ser-Tyr-Arg-Lys-Val-Leu-Ala-Gln-Leu-Ser-Ala-Arg-Lys-Leu-Leu-Gln-Asp-Ile-Leu-Ser-Arg-Hse-$NH_2$ or a non-toxic salt thereof.

14. A GRF PEPTIDE of claim 3 selected from the group consisting of $Val^2$ $Ser^8$ $Ala^{15}$ $Leu^{27}$ $Ser^{28}$ $Hse^{30}$ bGRF(1–30)$NH_2$, $Val^2$ $Ser^8$ $Ala^{15}$ $Leu^{28}$ $Ser^{28}$ $Hse^{30}$ bGRF(1–30)NH—$C_2H_5$, $Ile^2$ $Ser^8$ $Ala^{15}$ $Leu^{27}$ $Ser^{28}$ $Hse^{30}$ bGRF(1–30)$NH_2$, $Ile^2$ $Ser^8$ $Ala^{15}$ $Leu^{27}$ $Ser^{28}$ $Hse^{30}$ bGRF(1–30)NH—$C_2H_5$, $Val^2$ $Ser^8$ $Ala^{15}$ $Leu^{27}$ $Ser^{28}$ $Hse^{33}$ bGRF(1–33)$NH_2$, $Val^2$ $Ser^8$ $Ala^{15}$ $Leu^{27}$ $Ser^{28}$ $Hse^{33}$ bGRF(1–33)NH—$C_2H_5$, $Ile^2$ $Ser^8$ $Ala^{15}$ $Leu^{27}$ $Ser^8$ $Hse^{33}$ bGRF(1–33)$NH_2$, $Ile^2$ $Ser^8$ $Ala^{15}$ $Leu^{27}$ $Ser^{28}$ $Hse^{33}$ bGRF(1–33)NH—$C_2H_5$, $Thr^2$ $Ser^8$ $Ala^{15}$ $Leu^{27}$ $Ser^{28}$ $Hse^{30}$ bGRF(1–30)$NH_2$, $Thr^2$ $Ser^8$ $Ala^{15}$ $Leu^{27}$ $Ser^{28}$ $Hse^{30}$ bGRF(1–30)NH—$C_2H_5$, $Thr^2$ $Ser^8$ $Ala^{15}$ $Leu^{27}$ $Ser^{28}$ $Hse^{33}$ bGRF(1–33)$NH_2$, $Thr^2$ $Ser^8$ $Ala^{15}$ $Leu^{27}$ $Ser^{28}$ $Hse^{33}$ bGRF(1–33)NH—$C_2H_5$, $Val^2$ $Ser^8$ $Ala^{15}$ $Leu^{27}$ $Hse^{28}$ bGRF(1–28)$NH_2$, $Val^2$ $Ser^8$ $Ala^{15}$ $Leu^{27}$ $Hse^{28}$ bGRF(1–28)NH—$C_2H_5$, $Ile^2$ $Ser^8$ $Ala^{15}$ $Leu^{27}$ $Hse^{28}$ bGRF(1–28)$NH_2$, $Ile^2$ $Ser^8$ $Ala^{15}$ $Leu^{27}$ $Hse^{28}$ bGRF(1–28)NH—$C_2H_5$, $Thr^2$ $Ser^8$ $Ala^{15}$ $Leu^{27}$ $Hse^{28}$ bGRF(1–28)$NH_2$, and $Thr^2$ $Ser^8$ $Ala^{15}$ $Leu^{27}$ $Hse^{28}$ bGRF(1–28)NH—$C_2H_5$, or a non-toxic salt thereof.

15. A GRF PEPTIDE of claim 3 selected from the group consisting of $Thr^2$ $Ala^{15}$ $Leu^{27}$ bGRF(1–29)$NH_2$, $Val^2$ $Ala^{15}$ $Leu^{27}$ bGRF(1–29)$NH_2$, $Ile^2$ $Ala^{15}$ $Leu^{27}$ bGRF(1–29)$NH_2$, $Val^2$ $Ser^8$ $Ala^{15}$ $Leu^{27}$ $Ser^{28}$ $Hse^{45}$ bGRF(1–45)$NH_2$, $Ile^2$ $Ser^8$ $Ala^{15}$ $Hse^{27}$ bGRF(1–27)$NH_2$, $Thr^2$ $Val^{15}$ bGRF(1–29)$NH_2$, $Thr^2$ $Leu^{15}$ $Leu^{27}$ bGRF(1–29)$NH_2$, $Thr^2$ $Ile^{15}$ $Leu^{27}$ bGRF(1–29)$NH_2$, $Thr^2$ $Ser^8$ $Val^{15}$ $Leu^{27}$ $Ser^{28}$ $Hse^{30}$ bGRF(1–30)$NH_2$, $Thr^2$ $Ser^8$ $Ala^{15}$ $Ile^{27}$ $Ser^{28}$ bGRF(1–29)$NH_2$, $Thr^2$ $Ser^8$ $Leu^{15}$ $Leu^{27}$ $Ser^{28}$ $Hse^{30}$ bGRF(1–30)OH, and $Thr^2$ $Ser^8$ $Ile^{15}$ $Leu^{27}$ $Ser^{28}$ bGRF(1–40)OH, or a non-toxic salt thereof.

16. A method of stimulating the release of growth hormone in an animal, which comprises administering to said animal an effective amount of a GRF PEPTIDE having Thr, Val and Ile residue in place of the amino acid residue normally found at position 2 and having an amino acid selected from the group consisting of Ala, Val, Leu or Ile at position 15.

17. A method according to claim 16 wherein the GRF PEPTIDE has the formula R-$R_1$-$R_2$-$R_3$-Ala-Ile-Phe-Thr-$R_8$-Ser-Tyr-Arg-$R_{12}$-$R_{13}$-Leu-$R_{15}$-Gln-Leu-$R_{18}$-$R_{19}$-Arg-$R_{21}$-$R_{22}$-Leu-Gln-$R_{25}$Ile-$R_{27}$-$R_{28}$-Arg-Gln-Gln-Gly-Glu-$R_{34}$-$R_{35}$-Gln-Glu-$R_{38}$-$R_{39}$-$R_{40}$-Arg-$R_{42}$-Arg-Leu-Z wherein R is H, $C_1$–$C_5$ alkyl or benzyl;

$R_1$ is Tyr or His;

$R_2$ is Thr, Val or Ile;

$R_3$ is Asp, Glu or Cya;

$R_8$ is Asn or Ser;

$R_{12}$ is Lys or Arg, or N-ε-alkyl- or N-ε-benzyl-Lys when R is $C_1$–$C_5$ alkyl or benzyl;

$R_{13}$ is Val or Ile;

$R_{15}$ is Ala, Val, Leu or Ile;

$R_{18}$ is Ser or Tyr;

$R_{19}$ is Ala, Val or Ile;

$R_{21}$ is Lys or Arg, or N-ε-alkyl- or N-ε-benzyl-Lys when R is $C_1$–$C_5$ alkyl or benzyl;

$R_{22}$ is Ala or Leu;

$R_{25}$ is Asp or Glu;

$R_{27}$ is Met, Ile or Leu;

$R_{28}$ is Asn or Ser;

$R_{34}$ is Ser or Arg;

$R_{35}$ is Asn or Ser;

$R_{38}$ is Arg or Gln;

$R_{39}$ is Gly or Arg;

$R_{40}$ is Ala or Ser;

$R_{42}$ is Ala, Val or Phe; and

Z signifies the carboxyl moiety of the amino acid residue at the C-terminal and is the radical —$COOR_a$, —$CR_aO$, —$CONHNHR_a$, —$CON(R_a)(R_b)$ or —$CH_2OR_a$, with $R_a$ and $R_b$ being $C_1$–$C_8$ alkyl or hydrogen; or a biologically active fragment thereof extending from R at the N-terminus to a residue in any of positions 27 through 44 as its C-terminus; or a Hse(lactone), HseOH or HseN($R_a$)($R_b$) of the foregoing and/or a non-toxic salt of the foregoing.

18. A composition for stimulating the release of growth hormone in an animal comprising an effective amount of a GRF PEPTIDE of the formula R-$R_1$-$R_2$-$R_3$-Ala-Ile-Phe-Thr-$R_8$-Ser-Tyr-Arg-$R_{12}$-$R_{13}$-Leu-$R_{15}$-Gln-Leu-$R_{18}$-$R_{19}$-Arg-$R_{21}$-$R_{22}$-Leu-Gln-$R_{25}$-Ile-$R_{27}$-$R_{28}$-Arg-Gln-Gln-Gly-Glu-$R_{34}$-$R_{35}$-Gln-Glu-$R_{38}$-$R_{39}$-$R_{40}$-Arg-$R_{42}$-Arg-Leu-Z wherein R is H, $C_1$–$C_5$ alkyl or benzyl;

$R_1$ is Tyr or His;

$R_2$ is Thr, Val or Ile;

$R_3$ is Asp, Glu or Cya;

$R_8$ is Asn or Ser;

$R_{12}$ is Lys or Arg, or N-ε-alkyl- or N-ε-benzyl-Lys when R is $C_1$–$C_5$ alkyl or benzyl;

$R_{13}$ is Val or Ile;

$R_{15}$ is Ala, Val, Leu or Ile;

$R_{18}$ is Ser or Tyr;

$R_{19}$ is Ala, Val or Ile;

$R_{21}$ is Lys or Arg, or N-ε-alkyl- or N-ε-benzyl-Lys when R is $C_1$–$C_5$ alkyl or benzyl;

$R_{22}$ is Ala or Leu;

$R_{25}$ is Asp or Glu;

$R_{27}$ is Met, Ile or Leu;

$R_{28}$ is Asn or Ser;

$R_{34}$ is Ser or Arg;

$R_{35}$ is Asn or Ser;

$R_{38}$ is Arg or Gln;

$R_{39}$ is Gly or Arg;

$R_{40}$ is Ala or Ser;

$R_{42}$ is Ala, Val or Phe; and

Z signifies the carboxyl moiety of the amino acid residue at the C-terminal and is the radical —$COOR_a$, —$CR_aO$, —$CONHNHR_a$, —$CON(R_a)(R_b)$ or —$CH_2OR_a$, with $R_a$ and $R_b$ being $C_1$–$C_8$ alkyl or hydrogen; or a biologically active fragment thereof extending from R at the N-terminus to a residue in any of positions 27 through 44 as its C-terminus; or a Hse(lactone), HseOH or HseN($R_a$)($R_b$) of the foregoing and/or a non-toxic salt of the foregoing; in association with a pharmaceutically acceptable carrier.

\* \* \* \* \*